United States Patent
Margulis et al.

(10) Patent No.: US 11,033,383 B2
(45) Date of Patent: Jun. 15, 2021

(54) TYMPANOPLASTIC PATCH APPLICATOR

(71) Applicant: TYMCURE LTD, Caesarea (IL)

(72) Inventors: Ariel Margulis, Ramat Hasharon (IL); Mazal Dahan, Mazkeret Batya (IL); Nir Lilach, Kfar Yehoshua (IL); Eyal Aviram, Herzeliya (IL); Erez Zelnik, Caesarea (IL)

(73) Assignee: TYMCURE LTD., Caesarea (IL)

( * ) Notice: Subject to any disclaimer, the term of this patent is extended or adjusted under 35 U.S.C. 154(b) by 326 days.

(21) Appl. No.: 15/761,103

(22) PCT Filed: Sep. 19, 2016

(86) PCT No.: PCT/IB2016/055575
§ 371 (c)(1),
(2) Date: Mar. 18, 2018

(87) PCT Pub. No.: WO2017/046779
PCT Pub. Date: Mar. 23, 2017

(65) Prior Publication Data
US 2018/0263763 A1 Sep. 20, 2018

Related U.S. Application Data

(60) Provisional application No. 62/220,283, filed on Sep. 18, 2015, provisional application No. 62/220,122, filed on Sep. 17, 2015.

(51) Int. Cl.
*A61F 2/18* (2006.01)
*A61F 11/00* (2006.01)

(52) U.S. Cl.
CPC .............. *A61F 2/18* (2013.01); *A61F 11/002* (2013.01); *A61F 11/004* (2013.01); *A61F 2002/183* (2013.01)

(58) Field of Classification Search
CPC ...... A61F 2/18; A61F 2002/183; A61F 11/00; A61F 11/002; A61F 11/004;
(Continued)

(56) References Cited

U.S. PATENT DOCUMENTS

| 4,641,651 A | 2/1987 | Card |
| 5,180,391 A * | 1/1993 | Beoni ...................... A61F 2/18 623/10 |

(Continued)

FOREIGN PATENT DOCUMENTS

| CN | 2162943 | 4/1994 |
| GB | 108797 | 8/1917 |

(Continued)

OTHER PUBLICATIONS

Hennink, W.E. et al., "Novel crosslinking methods to design hydrogels", Advanced Drug Delivery Reviews, Jan. 17, 2002, vol. 54 Issue 1, pp. 13-36.
(Continued)

*Primary Examiner* — Diane D Yabut
*Assistant Examiner* — Christian D. Knauss
(74) *Attorney, Agent, or Firm* — The Roy Gross Law Firm, LLC; Roy Gross

(57) ABSTRACT

A tympanoplatic patch applicator comprising: a handle disposed with a deployment control; a deployment stem comprising multiple nested sleeves connected to the handle; a patch configured to be affixed to the distal end of the deployment stem via an actuation filament embedded in the deployment stem; and a filament-based deployment system controllable by the deployment control, wherein the deployment stem is configured to position the patch at the internal side of a perforated tympanic membrane in the middle ear by introducing the patch into the ear canal and penetrating the perforated tympanic membrane with the distal end of the
(Continued)

deployment stem, and wherein the filament-based deployment system is configured to release the patch from the distal end of the deployment stem, thereby deploying the patch on the internal side of the perforated tympanic membrane.

18 Claims, 36 Drawing Sheets

(58) Field of Classification Search
CPC ...... A61B 17/0057; A61B 2017/00575; A61B 2017/00592; A61B 2017/00597; A61B 2017/0061; A61B 2017/00623; A61B 2017/00628; A61B 2017/00632
See application file for complete search history.

(56) References Cited

U.S. PATENT DOCUMENTS

| | | | | |
|---|---|---|---|---|
| 5,236,455 | A * | 8/1993 | Wilk | A61F 2/18 128/890 |
| 5,254,133 | A * | 10/1993 | Seid | A61B 17/0057 128/899 |
| 5,501,700 | A | 3/1996 | Hirata | |
| 5,643,300 | A | 7/1997 | Hirata | |
| 5,643,317 | A * | 7/1997 | Pavcnik | A61B 17/0057 606/151 |
| 6,309,419 | B1 | 10/2001 | De Juan, Jr. et al. | |
| 2002/0151974 | A1 | 10/2002 | Bonassar et al. | |
| 2003/0078597 | A1 | 4/2003 | Blatter et al. | |
| 2004/0137033 | A1 | 7/2004 | Calhoun et al. | |
| 2004/0181185 | A1 | 9/2004 | Lee | |
| 2005/0245964 | A1 * | 11/2005 | Boudjemline | A61B 17/064 606/213 |
| 2005/0256532 | A1 * | 11/2005 | Nayak | A61B 17/0057 606/151 |
| 2007/0028927 | A1 | 2/2007 | Slattery et al. | |
| 2007/0066863 | A1 * | 3/2007 | Rafiee | A61B 17/0401 600/37 |
| 2008/0003205 | A1 | 1/2008 | Bonassar et al. | |
| 2008/0262468 | A1 | 10/2008 | Clifford et al. | |
| 2009/0297533 | A1 | 12/2009 | Lichter et al. | |
| 2009/0299379 | A1 | 12/2009 | Katz et al. | |
| 2013/0338678 | A1 | 12/2013 | Loushin et al. | |
| 2013/0345722 | A1 * | 12/2013 | Margulis | A61F 11/004 606/131 |
| 2014/0031645 | A1 | 1/2014 | Loushin et al. | |

FOREIGN PATENT DOCUMENTS

| | | | |
|---|---|---|---|
| JP | 2006240441 | 9/2006 | |
| KR | 20080040516 | 5/2008 | |
| WO | 2010062693 A2 | 6/2010 | |
| WO | 2012120513 A1 | 9/2012 | |
| WO | WO-2016005946 A2 * | 1/2016 | ....... A61B 17/00491 |

OTHER PUBLICATIONS

Truong Nguyen, Kytia et al., "Photopolymerizable hydrogels for tissue engineering applications", Biomaterials, Nov. 2002, vol. 23 issue 22, pp. 4307-4314.
N.A. Peppas et al "Hydrogels in pharmaceutical formulations", European Journal of Pharmaceutics and Biopharmaceutics, Jul. 2000, Col. 50 issue 2, pp. 27-46.
Schmedlen R. H. et al "Photocrosslinkable polyvinyl alcohol hydrogels that can be modified with cell adhesion peptides for use in tissue engineering", Biomaterials, Nov. 2002, vol. 23 Issue 22, pp. 4325-4332.
Notification of transmittal of the international search report and the written opinion of the international searching authority regarding PCT/IL2012/050076; dated Jun. 6, 2012, 13 pages.
Notification concerning transmittal of international preliminary report on patentability regarding PCT/IL2012/050076; dated Sep. 19, 2013, 8 pages.
Communication under rule 71(3) EPC from the European patent office regarding Application No. 12715440.9; dated Jul. 16, 2014, 6 pages.
"EpiDisc Tympanic Membrane Perforation Patch Kit", Medtronic, Nov. 14, 2014.
"EpiFilm and EpiDisc Otologic Laminae", Ear Packing Products Medtronic, Nov. 14, 2014.
"Procedures and Techniques for Tympanoplasty and Ossicular Reconstruction", Medtronic, Nov. 14, 2014.

* cited by examiner

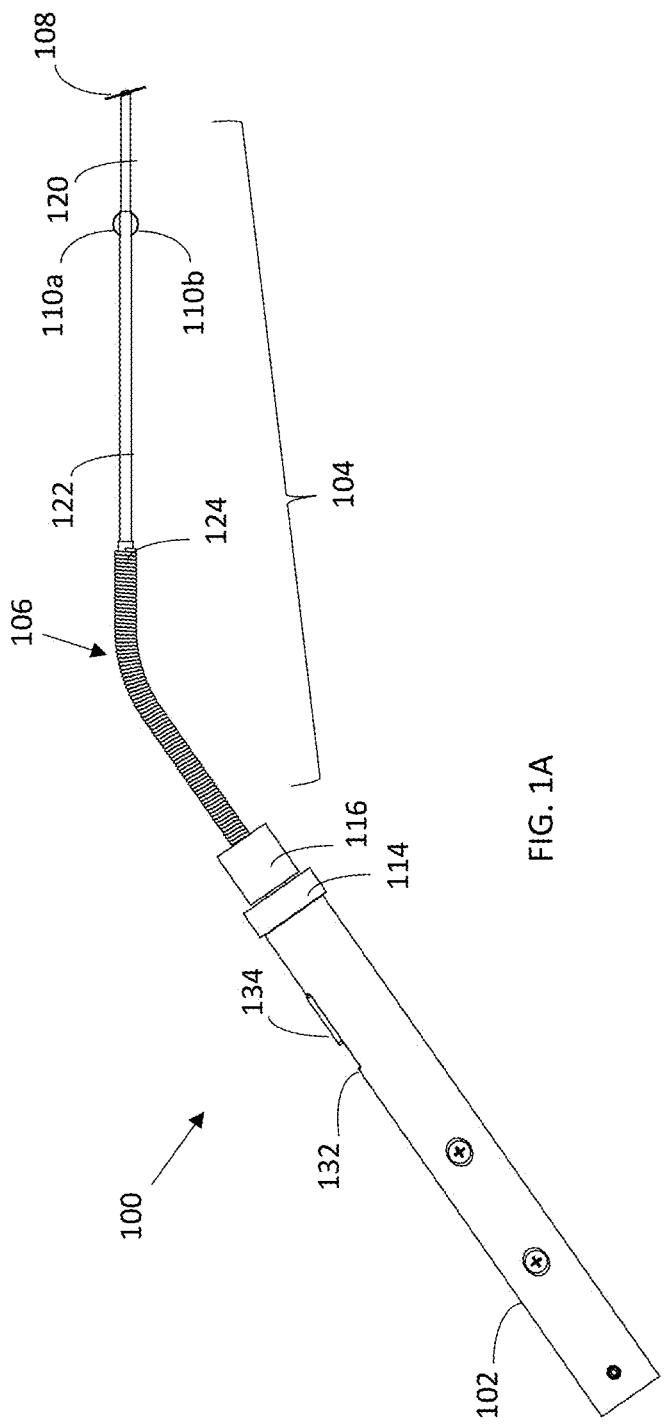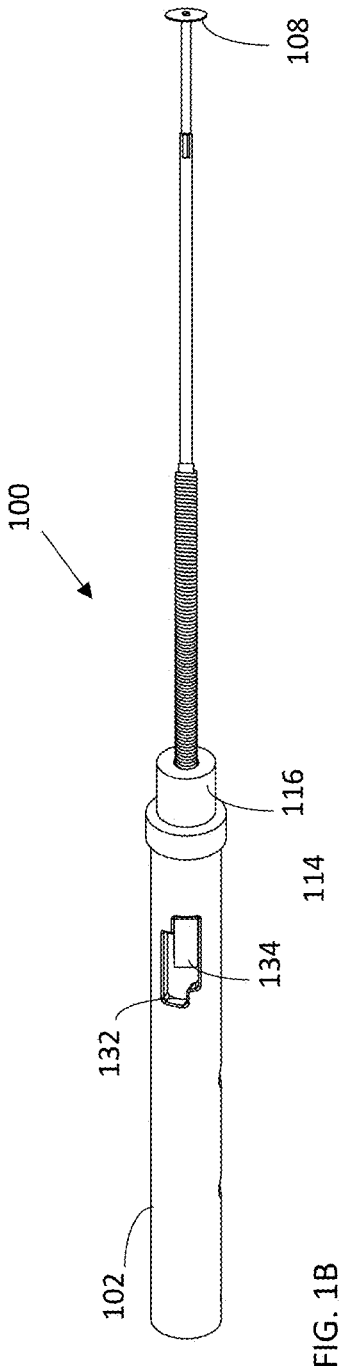

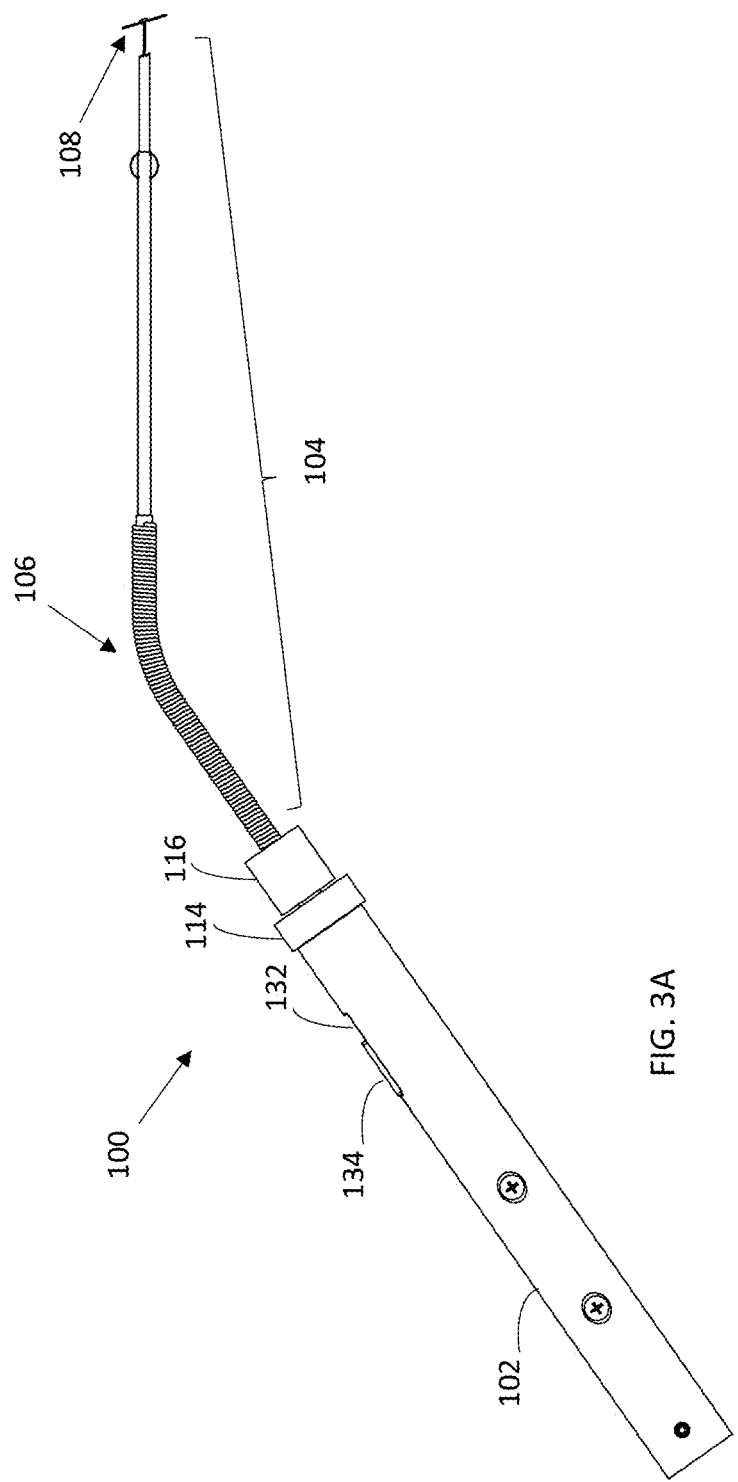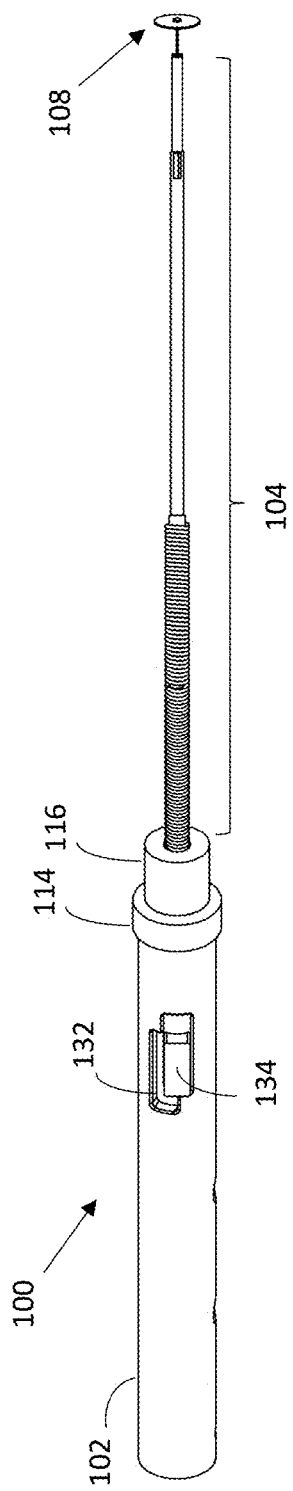
FIG. 3A
FIG. 3B

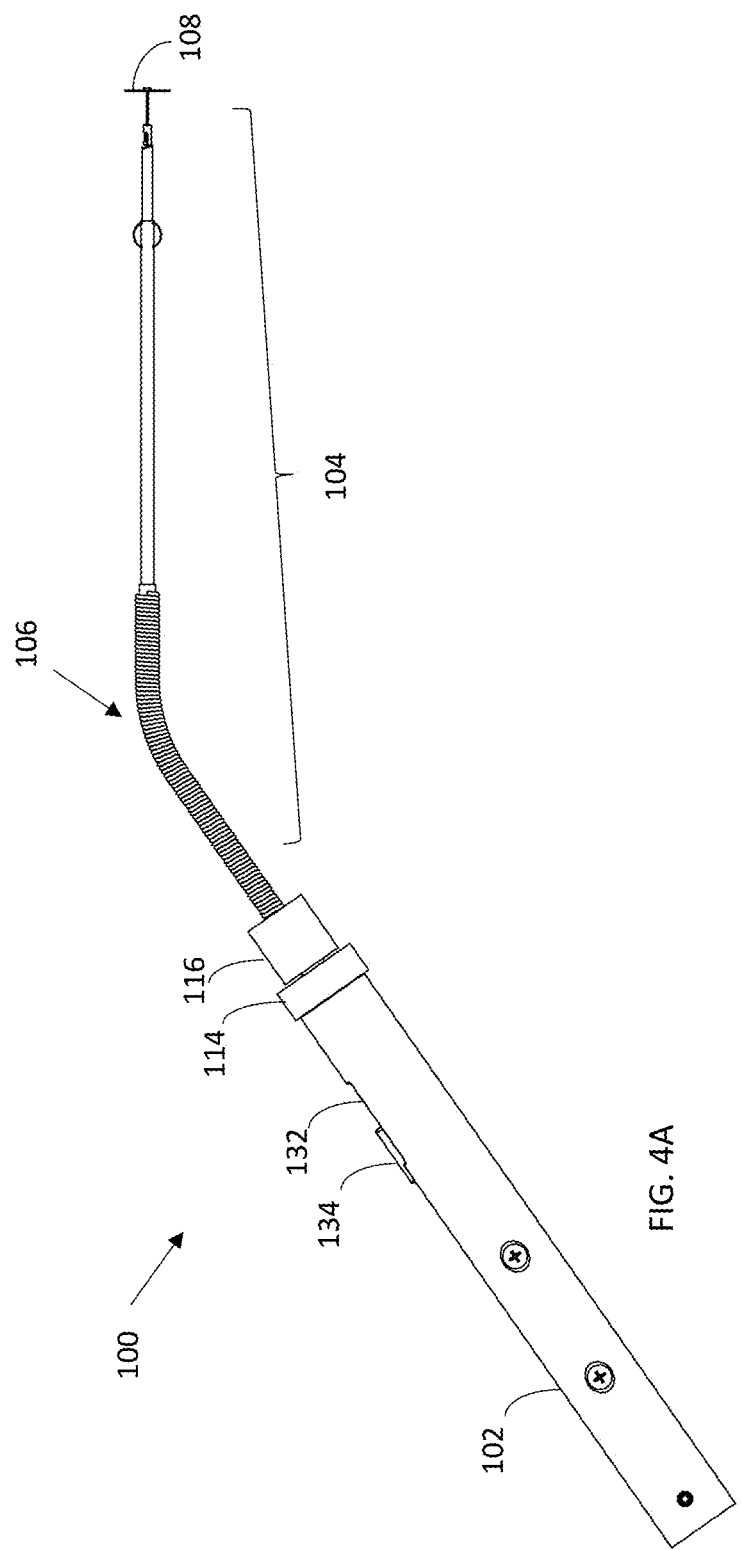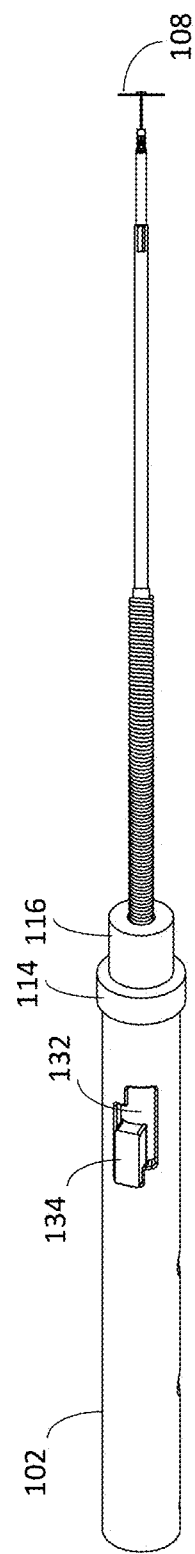
FIG. 4A
FIG. 4B

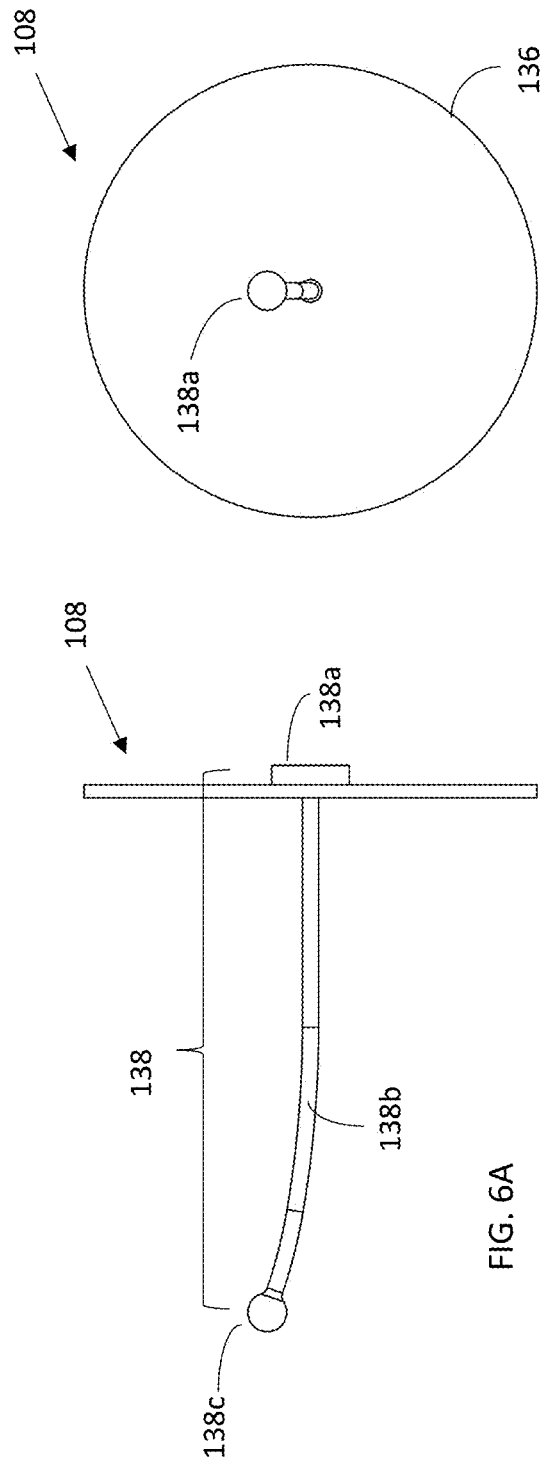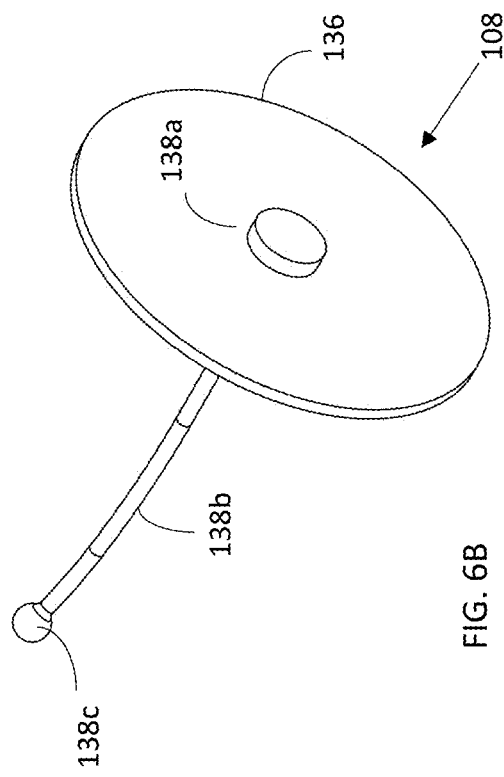

TYMPANOPLASTIC PATCH APPLICATOR

CROSS-REFERENCE TO RELATED PATENT APPLICATIONS

This application is a National Phase of PCT Patent Application No. PCT/IB2016/055575 having International filing date of Sep. 19, 2016, which claims the benefit of priority of U.S. Provisional Patent Application No. 62/220,283, filed Sep. 18, 2015 and entitled "Tympanoplastic Patch Applicator", and U.S. Provisional Patent Application No. 62/220,122, filed Sep. 17, 2015 and entitled "Tympanic Membrane Patch." The contents of the above applications are all incorporated by reference as if fully set forth herein in their entirety.

TECHNICAL FIELD

The invention relates to the field of tympanoplasty.

BACKGROUND

Tympanoplasty is a surgical treatment for repairing a perforation in the tympanic membrane (also known as the "eardrum") and defects in one or more of the ossicular bones. Perforation in the eardrum may be the result of a birth defect, or may be attributed to ear/nose/throat infections, physical ear injury, exposure to high noise levels, aging, etc.

A hole in the eardrum (tympanic membrane perforation) is a common consequence of an ear injury or an ear infection. These perforations are often surgically repaired for the sake of preventing further complications and improve hearing. Young kids as well as adults and also elderly people can suffer from tympanic membrane perforation. The exact number of surgical tympanic membrane perforation (TMP) performed each year is unknown.

One of the major causes for perforation in the eardrum is recurrent ear infections. The eardrum (tympanic membrane) becomes "scarred" with less blood supply than normal tissue. As such, it is less resistant to infection and eventually, a point may come that the eardrum, when faced with the stress of an abscess, dissolves away, leaving a hole in the eardrum.

Moreover, the eardrum may also become perforated by trauma caused by foreign objects. Although many traumatic perforations heal spontaneously, many require repair. Perforations may also occur following extrusion of pressure equalization tubes placed to prevent recurrent middle ear infections.

Chronic Eustachian tube problems cause negative middle ear pressures that can retract and thin the eardrum so much that it stops working as a sound collector and threatens to form cholesteatoma. In these cases, the collapsed sections of eardrum are removed surgically and repaired.

A hole in the eardrum leads to hearing loss because the eardrum no longer has the surface area to collect all of the sound coming into the ear. The magnitude of hearing loss is directly related to the size of the perforation.

An ear with a hole in the eardrum is highly susceptible to develop infections because as the endogenous barrier against moisture is perforated. Moisture evaporating from the exposed linings of the middle ear also tends to humidify the ear canal and creates a good environment for bacteria and fungi to grow.

Excessive humidity in the ear canal with recurrent infection is a common problem for hearing aid users. The hearing aid acts as a plug that keeps the ear from drying out, and promotes an environment for infection.

A small hole in the eardrum can sometimes be repaired by a procedure called myringoplasty. This is performed by irritating the margins of the perforation and then giving it some sort of template to grow across. Often, a small piece of tissue such as a piece of fat can be placed through the very small perforation and result in a successful closure.

Tympanoplasty: If a hole in the eardrum fails myringoplasty or is too large to repair with myringoplasty, then tympanoplasty is required. It is often performed by trimming the margins of the perforation and creating a patch out of the covering of the temporalis muscle above the ear.

In tympanoplasty, the graft material has to be held against the edges of the perforation until healing occurs. This generally takes a minimum of several weeks. Because the surgical area is too small to sew the graft into place, the graft and eardrum are sandwiched together between a mass of gelatin packing placed in the middle ear beneath the graft and in the ear canal over the graft.

SUMMARY

The following embodiments and aspects thereof are described and illustrated in conjunction with systems, tools and methods which are meant to be exemplary and illustrative, not limiting in scope.

There is provided, in accordance with an embodiment, a tympanoplatic patch applicator comprising: a handle disposed with a deployment control; a deployment stem comprising multiple nested sleeves connected to the handle; a patch configured to be affixed to the distal end of the deployment stem via an actuation filament embedded in the deployment stem; and a filament-based deployment system controllable by the deployment control, wherein the deployment stem is configured to position the patch at the internal side of a perforated tympanic membrane in the middle ear by introducing the patch into the ear canal and penetrating the perforated tympanic membrane with the distal end of the deployment stem, and wherein the filament-based deployment system is configured to release the patch from the distal end of the deployment stem, thereby deploying the patch on the internal side of the perforated tympanic membrane.

In some embodiments, the multiple nested sleeves include an inner sleeve, wherein the actuation filament is embedded within the inner sleeve.

In some embodiments, the multiple nested sleeves include a middle sleeve encasing the inner sleeve, wherein the patch is configured to be affixed at the distal end of the middle sleeve, thereby being affixed at the distal end of the deployment stem.

In some embodiments, the distal end of the middle sleeve is serrated to secure the position of the patch and prevent its rotation with respect to the middle sleeve, wherein a first activation of the deployment control causes the serrated distal end of the middle sleeve to withdraw proximally from the patch, thereby releasing the patch from the distal end of the middle sleeve.

In some embodiments, the distal end of the middle sleeve is beveled such that the patch is affixed at an angle that is non-perpendicular to the longitudinal axis of the middle sleeve, thereby allowing the orientation of the patch to align with the orientation of the perforated tympanic membrane.

In some embodiments, the tympanoplatic patch application further comprises a posture adjustor configured with the handle, wherein the posture adjustor is configured to align the orientation of the patch with the orientation of the perforated tympanic membrane.

In some embodiments, the deployment stem is bent, and further comprises a first spring configured to transfer an adjustment of the posture adjustor to a corresponding adjustment of the orientation of the patch over the bend.

In some embodiments, the filament-based deployment system comprises an exposable distal end of the inner sleeve, wherein the patch is disposed with a proximally positioned cord configured to extend from the distal end of the middle sleeve and engage with the actuation filament at the exposable distal end of the inner sleeve, thereby affixing the patch at the distal end of the middle sleeve when the exposable distal end of the inner sleeve is encased within the middle sleeve, and wherein a second activation of the deployment control causes the middle sleeve to withdraw proximally with respect to the inner sleeve and expose the exposable distal end, allowing the cord to disengage from the actuation filament to release the patch from the tympanoplatic patch applicator.

In some embodiments, the proximal end of the cord comprises a first bulge, and the distal end of the actuation filament comprises a second bulge, wherein positioning the first bulge proximal to the second bulge at the exposable distal end of the inner sleeve engages the cord with the actuation filament, and wherein exposing the exposable distal end of the inner sleeve allows the first bulge to slide distally over the second bulge, thereby disengaging the cord from the actuation filament.

In some embodiments, the deployment control is provided with a safety mechanism configured to prevent an accidental second activation of the deployment control.

In some embodiments, the tympanoplatic patch applicator further comprises a debridement mechanism, comprising: a debridement actuator configured with the handle, an outer sleeve of the multiple nested sleeves encasing the middle sleeve, and at least one protruding blade disposed at a distal end of the outer sleeve, where the actuator is configured to advance the outer sleeve relative to the middle sleeve until the blade reaches the distal end of the deployment stem, rotate the outer sleeve relative to the middle sleeve, thereby rotating the protruding blade and causing a debridement of the circumference of the perforation, and retract the outer sleeve relative to the middle sleeve.

In some embodiments, the debridement mechanism further comprises a niche configured to collect debrided tissue.

In some embodiments, a curvature of the at least one protruding blade controls a penetration depth of the blade into the perforation.

In some embodiments, the debridement mechanism further comprises a penetration depth controlling mechanism that limits the penetration depth of the at one protruding blade by limiting the advancement of the outer sleeve relative to the middle sleeve.

In some embodiments, the deployment stem is bent, and wherein the debridement actuator is configured to advance and retract the outer sleeve relative to the middle sleeve over the bend.

In some embodiments, the deployment stem further comprising a second spring configured to transfer a motion of the debridement actuator to the outer sleeve over the bent deployment stem, thereby enabling the advancement and retraction of the outer sleeve relative to the middle sleeve over the bend.

In some embodiments, the patch is constructed from a resilient material that flexes to fit through the perforation, and restores its original shape when emerging in the middle ear at the internal side of the tympanic membrane.

There is provided, in accordance with an embodiment, a method for deploying a patch at the internal side of a perforated tympanic membrane, comprising: introducing a patch, affixed to the distal end of a distally disposed stem of an applicator, into an ear canal; penetrating a perforation of a tympanic membrane with the patch; using a deployment control provided with a proximally disposed handle of the applicator to maneuver a filament-based deployment system that releases the patch from the distal end of the stem at the internal side of the tympanic membrane; and deploying the patch on the internal side of the perforated tympanic membrane.

In some embodiments, while the patch is positioned at the internal side of the tympanic membrane, aligning the orientation of the patch with the orientation of the perforated tympanic membrane using a posture adjustor provided with the proximally disposed handle of applicator.

In some embodiments, using the posture adjustor comprises rotating the posture adjustor to rotate a middle sleeve of the applicator, wherein the patch is secured to a beveled distal end of the middle sleeve.

In some embodiments, the method further comprises activating a debridement mechanism to debride dead tissue from the circumference of the perforation, and wetting the circumference of the debrided perforation with fresh blood released by the debriding.

In some embodiments, activating the debridement mechanism comprises using a debriding actuator disposed with the proximally disposed handle of the applicator to advance at least one debridement blade to the distal end of the stem, and rotate the at least one blade about the circumference of the perforation.

In some embodiments, the method further comprises collecting the removed tissue in a niche of the applicator, and preventing the removed tissue from reaching the middle ear.

In some embodiments, the method further comprises removing the at least one blade from the perforation by using the debridement actuator to retract the at least one blade from the distal end of the applicator.

In some embodiments, using the deployment control to maneuver the filament-based deployment system comprises detaching the patch from a serrated distal tip of the stem in a first detachment stage.

In some embodiments, deploying comprises pulling the patch proximally to come into contact with the internal side of the tympanic membrane by pulling the applicator proximally, and securing the patch to the tympanic membrane using the fresh blood as a glue.

In some embodiments, using the deployment control to maneuver the filament-based deployment system comprises decoupling a cord of the patch from a filament of the applicator in a second detachment stage.

There is provided, in accordance with an embodiment, a biodegradable patch construct having a first thickness and a second thickness.

In some embodiments, the second thickness is from 1.2 to 10 times thicker than said first thickness.

In some embodiments, the biodegradable patch further comprising an upper portion and a bottom portion.

In some embodiments, 0.5% to 20% of the surface area of the upper portion, the surface area bottom portion, or both comprises a projection.

In some embodiments, said bottom portion is a uniform surface.

In some embodiments, said upper portion comprises a projection.

In some embodiments, the surface area of the upper portion, the surface area of the bottom portion, or both comprises a cell adhesion molecule.

In some embodiments, the surface area of the upper portion, the surface area bottom portion, or both comprises an anti-inflammatory agent, an antibacterial agent, an antiseptic agent, a healing enhancing agent or any combination thereof.

In some embodiments, said patch is freeze-dried.

In some embodiments, the surface area of the upper portion, the surface area of the bottom portion, or both comprises a chondrocyte, a fibroblast, a chondrocyte precursor, a fibroblast precursor, or any combination thereof.

In some embodiments, the biodegradable patch comprises a hydrogel.

In some embodiments, said hydrogel is selected from the group consisting of polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly (methacrylic acids), copolymers of acrylic acid and methacrylic acid, poly(vinyl acetate), and sulfonated polymers.

In some embodiments, said hydrogel is selected from the group consisting of alginate, chitosan, pluronic, collagen, cellulose, agarose and any modification thereof.

There is provided, in accordance with an embodiment, a kit comprising a biodegradable patch as disclosed above, suspended in a sterile wetting solution, and instructions for use in repairing a perforation in a tympanic membrane in a mammal.

There is provided, in accordance with an embodiment, a method of repairing a perforation in a tympanic membrane in a mammal, the method comprising: providing biodegradable patch of claim 28 and implanting the biodegradable patch of claim 28 in the tympanic membrane in the mammal.

In some embodiments, said biodegradable patch of claim 28 is the biodegradable patch of any one of claims 29 to 40.

There is provided, in accordance with an embodiment, a tympanoplatic patch applicator comprising: a distally disposed handle configured with a deployment control mechanism; a proximally disposed deployment stem comprising multiple nested sleeves connected to the handle; two patches, comprising a distally disposed patch superimposed with a proximally disposed patch, wherein the distally disposed patch is configured to be affixed to the distal end of the deployment stem via a distal filament embedded in the deployment stem, and wherein the proximally disposed patch is configured to be affixed to the distal end of the deployment stem via a proximal filament embedded in the deployment stem; and a filament-based deployment system controllable by the deployment control mechanism, wherein the deployment stem is configured to introduce the two patches into the ear canal and penetrate the perforated tympanic membrane with at least the distally disposed patch, and wherein the filament-based deployment system is configured to: deploy the distally disposed patch at the internal side of the perforated tympanic membrane in the middle ear, and deploy the proximally disposed patch at the external side of the perforated tympanic membrane in the outer ear, thereby sandwiching the tympanic membrane between the distally disposed patch and the proximally disposed patch.

In some embodiments, the multiple nested sleeves include an inner sleeve and a middle sleeve encasing the inner sleeve, wherein the distal actuation filament is embedded within the inner sleeve thereby affixing the distal patch to the distal end of the inner sleeve, and wherein the proximal actuation filament is embedded within the middle sleeve, thereby affixing the proximal patch to the distal end of the middle sleeve.

In some embodiments, the deployment control mechanism comprises a first deployment actuator disposed on the handle, wherein the first deployment actuator is configured to retract and advance the middle sleeve relative to the inner sleeve.

In some embodiments, the deployment stem is further configured penetrate the perforated tympanic membrane with the proximally disposed patch, retract the proximal patch from the middle ear through the perforation of the tympanic membrane by retracting the middle sleeve relative to the inner sleeve using the first deployment actuator, and position the proximal patch at the external side of the perforated tympanic membrane in the outer ear, by advancing the middle sleeve relative to the inner sleeve using the first deployment actuator, thereby positioning the proximal patch against the external side of the perforated tympanic membrane.

In some embodiments, the deployment control mechanism comprises a second deployment actuator configured to release the distal patch and the proximal patch from the deployment stem.

In some embodiments, the distal patch is disposed with a distal patch cord configured to engage with the distal filament by looping the proximal end of the distal patch cord over the distal end of the distal filament in the inner sleeve, and wherein the proximal patch is disposed with a proximal patch cord configured to engage with the proximal filament by looping the proximal end of the proximal patch cord over the distal end of the proximal filament in the middle sleeve, wherein the filament-based deployment system comprises: a first filament locking boss configured to anchor the proximal end of the distal filament to the handle, and a second filament locking boss configured to anchor the proximal end of the proximal filament to the handle, wherein the second deployment actuator is connected to the first and second filament locking bosses, wherein activating the second deployment actuator retracts the distal and proximal filaments, causing the distal patch cord to disengage from the distal filament and the proximal patch cord to disengage from the proximal filament.

In some embodiments, the deployment control mechanism comprises a debridement actuator configured to control a debridement system, comprising: an outer sleeve of the multiple nested sleeves encasing and connected to the middle sleeve, and at least one protruding blade disposed at a distal end of the outer sleeve, wherein the debridement actuator is configured to rotate the outer sleeve, thereby rotating the protruding blade and causing a debridement of the circumference of the perforation, wherein the first deployment actuator is configured to retract and advance the outer sleeve with the middle sleeve.

In some embodiments, the debridement mechanism further comprises a niche configured to collect debrided tissue.

In some embodiments, a curvature of the at least one protruding blade controls a penetration depth of the blade into the perforation.

In some embodiments, the debridement mechanism further comprises a penetration depth controlling mechanism that limits the penetration depth of the at one protruding blade by limiting the advancement of the outer sleeve relative to the middle sleeve.

In some embodiments, the penetration depth controlling mechanism comprises the first deployment actuator.

In some embodiments, the debridement mechanism further comprises a power supply, a motor, and a gear wheel mechanically connecting the motor to the outer sleeve, wherein the debridement control is configured to control the power supply to activate the motor and turn the gear wheel, wherein turning the gear wheel causes the outer sleeve to rotate with the debridement blade.

In some embodiments, the deployment stem is bent, and wherein the first deployment actuator is configured to advance and retract the outer sleeve relative to the middle sleeve over the bend.

In some embodiments, the two patches are constructed from a resilient material that flexes to fit through the perforation, and restores its original shape when emerging from the perforation.

There is provided, in accordance with an embodiment, a tympanoplatic patch applicator comprising: a distally disposed handle configured with a deployment actuator; a proximally disposed deployment stem connected to the handle; two patches, comprising a distally disposed patch superimposed with a proximally disposed patch, wherein the distally disposed patch is configured to be affixed to the distal end of the deployment stem, and wherein the proximally disposed patch is configured to be affixed to the distal end of the deployment stem; and a deployment mechanism controllable by the deployment actuator, wherein the deployment stem is configured to introduce the two patches into the ear canal and penetrate the perforated tympanic membrane with at least the distally disposed patch, and wherein the deployment mechanism is configured to: deploy the distally disposed patch at the internal side of the perforated tympanic membrane in the middle ear, and deploy the proximally disposed patch at the external side of the perforated tympanic membrane in the outer ear, thereby sandwiching the tympanic membrane between the distally disposed patch and the proximally disposed patch.

There is provided, in accordance with an embodiment, a method for repairing a tympanic membrane, comprising: introduce two patches, comprising a distally disposed patch superimposed with a proximally disposed patch, into an ear canal via a deployment stem, wherein the distally disposed patch is affixed to the distal end of the deployment stem via a distal filament embedded in the deployment stem, and wherein the proximally disposed patch is affixed to the distal end of the deployment stem via a proximal filament embedded in the deployment stem; penetrating the perforated tympanic membrane with at least the distally disposed patch; deploying the distally disposed patch at the internal side of the perforated tympanic membrane in the middle ear; and deploy the proximally disposed patch at the external side of the perforated tympanic membrane in the outer ear, thereby sandwiching the tympanic membrane between the distally disposed patch and the proximally disposed patch.

In some embodiments, the deployment stem comprises an inner sleeve wherein the distal actuation filament is embedded within the inner sleeve thereby affixing the distally disposed patch to the distal end of the inner sleeve, wherein penetrating the perforated tympanic membrane with at least the distally disposed patch comprises penetrating the perforated tympanic membrane with at least the inner sleeve.

In some embodiments, the deployment stem further comprises a middle sleeve encasing the inner sleeve, wherein the proximal actuation filament is embedded within the middle sleeve, thereby affixing the proximal patch to the distal end of the middle sleeve, the method further comprising: penetrating the perforated tympanic membrane with both the distally disposed patch together with the proximally disposed patch by inserting the middle sleeve encasing the inner sleeve through the perforation, retracting the proximal patch from the middle ear through the perforation of the tympanic membrane by retracting the middle sleeve relative to the inner sleeve, and positioning the proximal patch at the external side of the perforated tympanic membrane in the outer ear.

In some embodiments, the method further comprises retracting the deployment stem until the distally disposed patch is flush with the internal side of the perforated tympanic membrane, thereby deploying the distally disposed patch.

In some embodiments, the method further comprises advancing the middle sleeve relative to the inner sleeve until the proximally disposed patch is flush against the external side of the perforated tympanic membrane, thereby deploying the proximally disposed patch.

In some embodiments, the distally disposed patch is disposed with a distal patch cord configured to engage with the distal filament by looping the proximal end of the distal patch cord over the distal end of the distal filament in the inner sleeve, and wherein the proximally disposed patch is disposed with a proximal patch cord configured to engage with the proximal filament by looping the proximal end of the proximal patch cord over the distal end of the proximal filament in the middle sleeve, the method further comprising exerting a tension on the distal and proximal filaments to disengage the distal patch cord from the distal filament and the proximal patch cord from the proximal filament, and release the distally disposed patch and the proximally disposed patch from the deployment stem.

In some embodiments, the method further comprises, prior to deploying the distally disposed patch and the proximally disposed patch, performing a debridement of a circumference of the perforation of the tympanic membrane, wherein deploying the distally disposed patch and the proximally disposed patch further comprises gluing the distally disposed patch and the proximally disposed patch to the perforated tympanic membrane using blood released from the debridement.

In some embodiments, the method further comprises collecting debrided tissue resulting from the debridement.

In some embodiments, performing the debridement comprises: penetrating the perforated tympanic membrane with an outer sleeve encasing the middle sleeve and the inner sleeve, wherein the outer sleeve is disposed with a debridement blade, rotating the outer sleeve, thereby rotating the debridement blade about the circumference of the perforation, and evacuating the outer and middle sleeves from the middle ear by retracting the outer sleeve together with the middle sleeve through the perforation.

In some embodiments, the method further comprises controlling a penetration depth of the at one protruding blade by limiting the advancement of the outer sleeve relative to the inner sleeve.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 1A-1I, show various views of a tympanoplatic patch applicator, in accordance with an embodiment;

FIGS. 3A-3F show various views of the tympanoplatic patch applicator of FIGS. 1A-1I in a follow-up deployment stage, in accordance with an embodiment;

FIGS. 4A-4F show various views of the tympanoplatic patch applicator of FIGS. 1A-1I in another follow-up deployment stage, in accordance with an embodiment;

FIGS. 6A-6C show various views of a tympanoplatic patch, in accordance with an embodiment;

DETAILED DESCRIPTION

Disclosed herein is a tympanoplatic patch applicator configured for transcanal approach, and a method for operating the same.

The applicator may introduce at least one biocompatible, and optionally biodegradable patch through a perforation in the tympanic membrane, and deploy the patch over the perforation from the inner side of the tympanic membrane— inside the middle ear. Optionally, the applicator includes a debridement mechanism that removes dead tissue from the circumference of the perforation, wets the circumference with fresh blood, and collects the removed tissue to prevent it from reaching the middle ear.

Figure 1C:
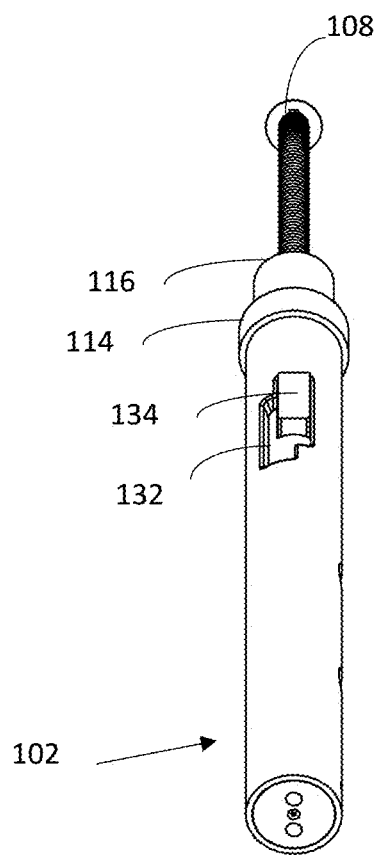
Figure 1D:
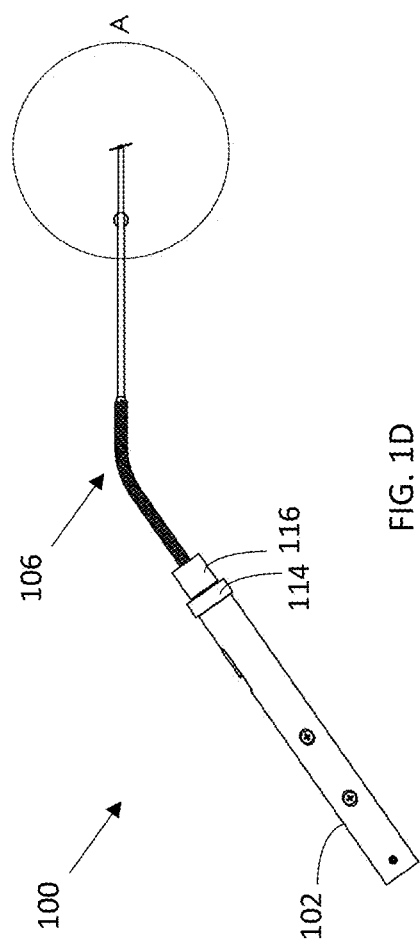
Figure 1E:
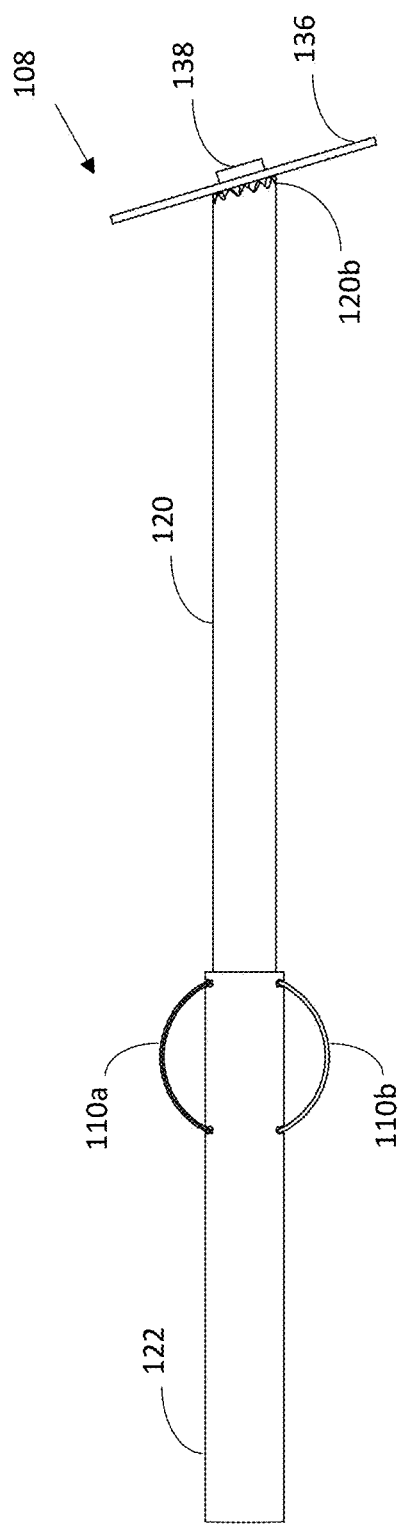

Reference is now made to FIGS. 1A-1I, which show various views of a tympanoplatic patch applicator 100, in accordance with an embodiment. FIG. 1A shows a side view of applicator 100 and FIGS. 1B-1C show two top views of applicator 100. FIG. 1D shows a side view similar to FIG. 1A, and FIG. 1E shows a detail of section A of FIG. 1D.

Applicator 100 generally includes a proximally disposed handle 102 configured with a deployment control, such as a button 134 moveable within a niche 132. Handle 102 may be connected to a distally disposed deployment stem 104 which extends from handle 102, and may be operated so as to deploy a biocompatible optionally biodegradable patch 108 over a perforation in the tympanic membrane. Optionally, patch 108 may be affixed to the distal end of deployment stem 104 via an actuation filament 126 embedded in the deployment stem 104, and will be described in greater detail below. An actuator 114 and actuator 116 may be provided at the proximal end of stem 104 connecting to the distal end of handle 102 for controlling the deployment of patch 108.

Figure 1F:
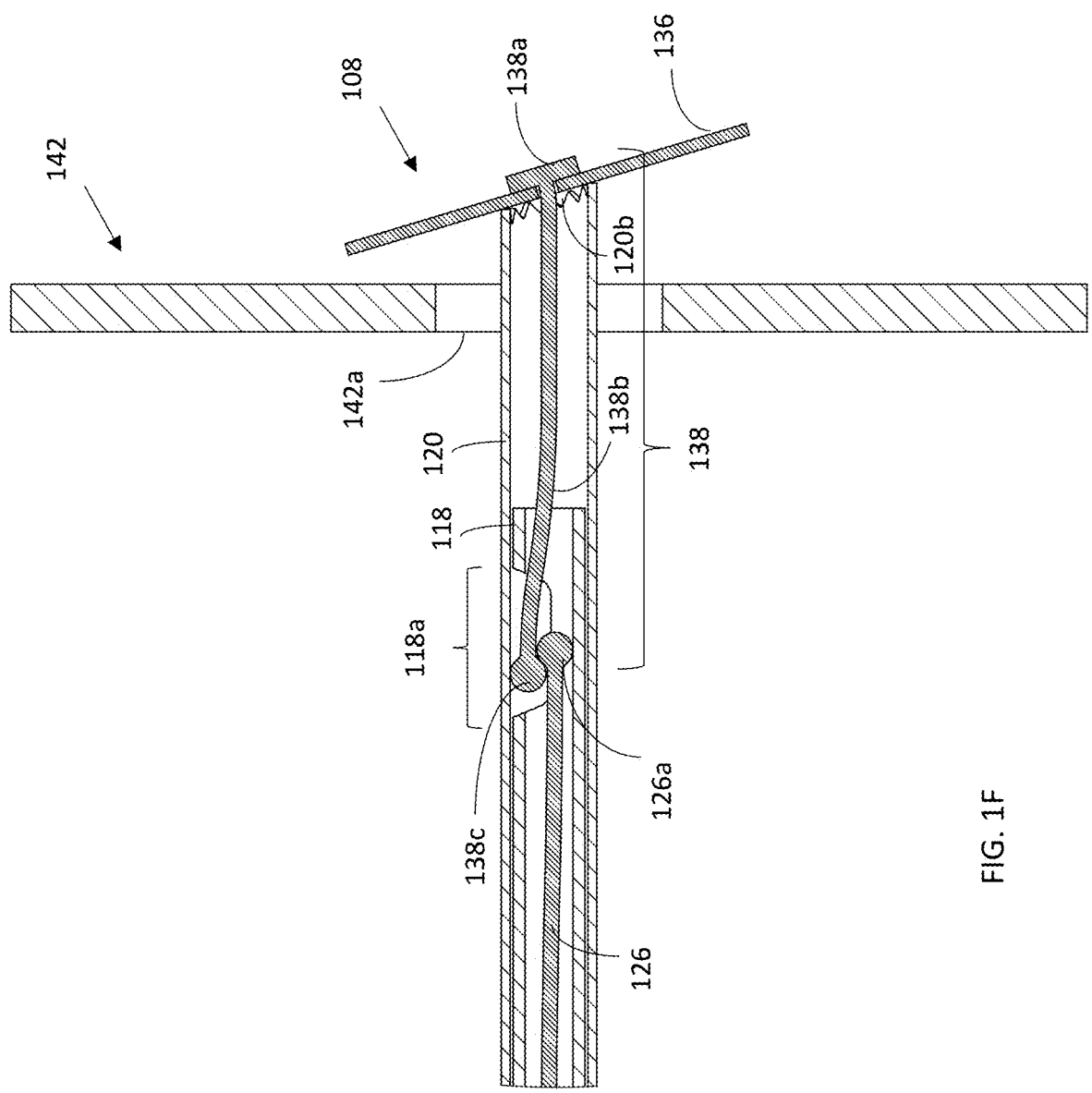

Stem 104 may position patch 108 at the internal side of a perforated tympanic membrane 142 in the middle ear by introducing patch 108 into the ear canal and penetrating the perforated tympanic membrane with the distal end of the deployment stem 104, such as illustrated in FIG. 1F. A deployment mechanism provided with applicator 100, such as may be filament-based, may release patch 108 from the distal end of deployment stem 104 while it's positioned at the internal side of the tympanic membrane, to deploy the patch 108 on the internal side of the perforated tympanic membrane.

The deployment control, provided with proximally disposed handle 102 of applicator 100, may be used by a surgeon to maneuver the filament-based deployment system to release patch 108 from the distal end of applicator 100 at the internal side of the tympanic membrane. Thus, patch 108 may be deployed on the internal side of the perforated tympanic membrane using the proximally disposed deployment control provided on handle 102.

Button 134 may have three positions within niche 132: A distal position at the beginning of the deployment, shown in FIGS. 1A-1C and 2A-2C, a middle position that implements a first stage for releasing patch 108 from stem 104, shown in FIGS. 3A-3C, and a proximal position that implements a second stage for releasing patch 108 from stem 104, shown in FIGS. 4A-4C.

Figure 1G:
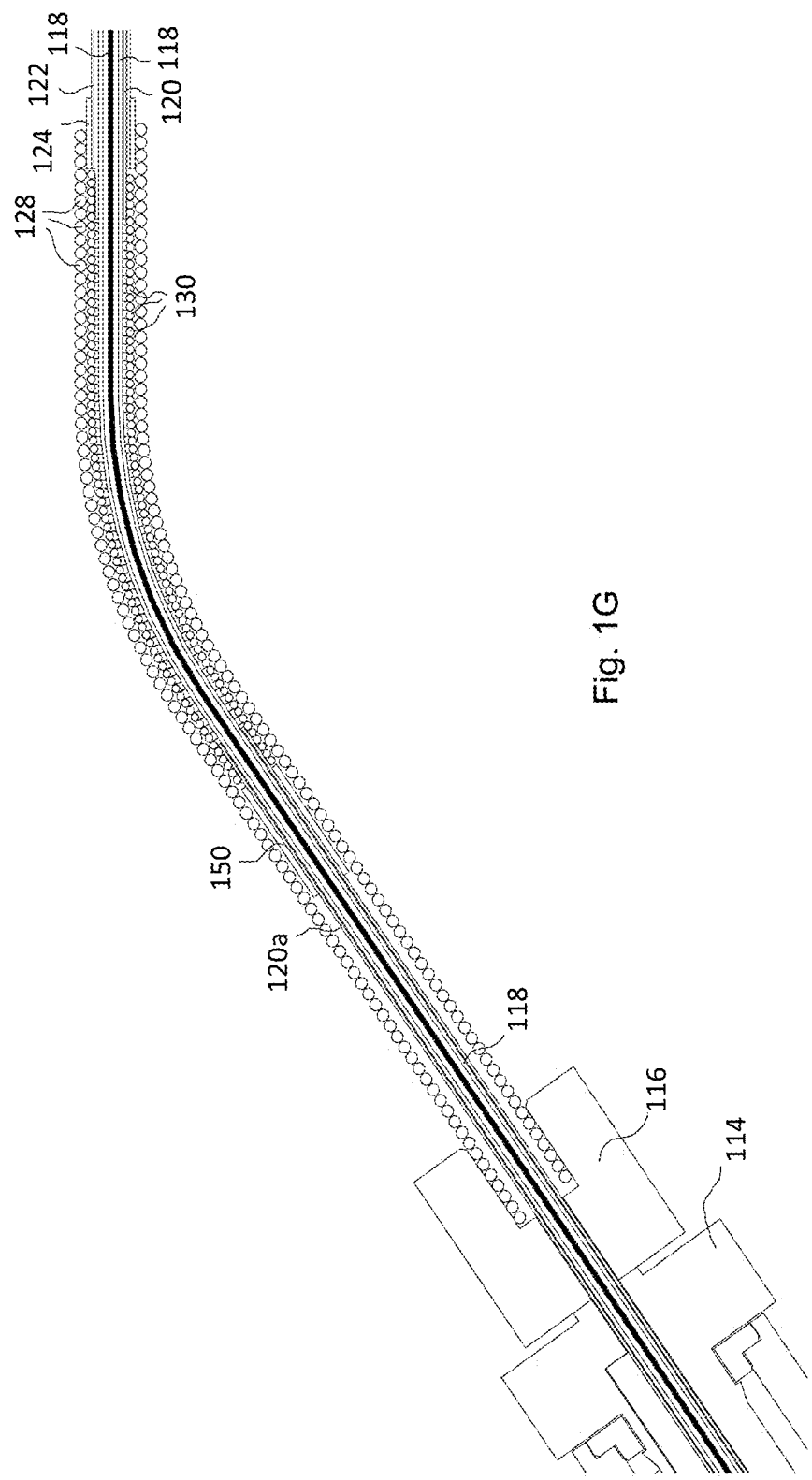

Referring to FIG. 1G, stem 104 may be include multiple nested sleeves and substantially concentric cylindrical sleeve, such as an inner sleeve 118, encased within a middle sleeve 120, which is encased within an outer sleeve 122. The multiple sleeves may be telescoping, and may slide longitudinally with respect to each other, allowing each sleeve to advance and retract accordingly.

Optionally, patch 108 is affixed, or supported, at the distal end of middle sleeve 120 encasing inner sleeve 118, thereby being affixed to, or supported at, the distal end of the deployment stem 104. Referring to FIG. 1F, a detailed view of the distal end of middle sleeve 120 is shown. Optionally, the distal end 122b of middle sleeve 120 is serrated to secure the position and/or orientation of patch 108 at distal end 122b, and prevent or reduce its rotation with respect to the middle sleeve 120.

Optionally, the distal end 120b of middle sleeve 120 is beveled, or cut at an angle, such that patch 108 is affixed at an angle that is non-perpendicular to the longitudinal axis of middle sleeve 120. This may allow aligning the orientation of the patch 108 with the posture, or orientation, of the perforated tympanic membrane.

Optionally, inner sleeve 118 extends along the full length of stem 104, serving as its rigid core. Inner sleeve 118 may be bent, resulting in a corresponding bend in stem 104 at an area denoted 106, shown in FIG. 1A, allowing the distal end of stem 104 to be at a different height than the proximal end of handle 102. Bend 106 may improve a surgeon's control during the deployment of patch 108 by preventing or reducing an obstruction of the line of vision to the distal end of stem 104 due to the surgeon's hand holding the applicator 100 by handle 102. Thus, when the surgeon grasps handle 102 and inserts stem 104 into a patient's ear canal, the handle 102 and the surgeon's hand do not block his or her view of the canal's internals.

Figure 1H:
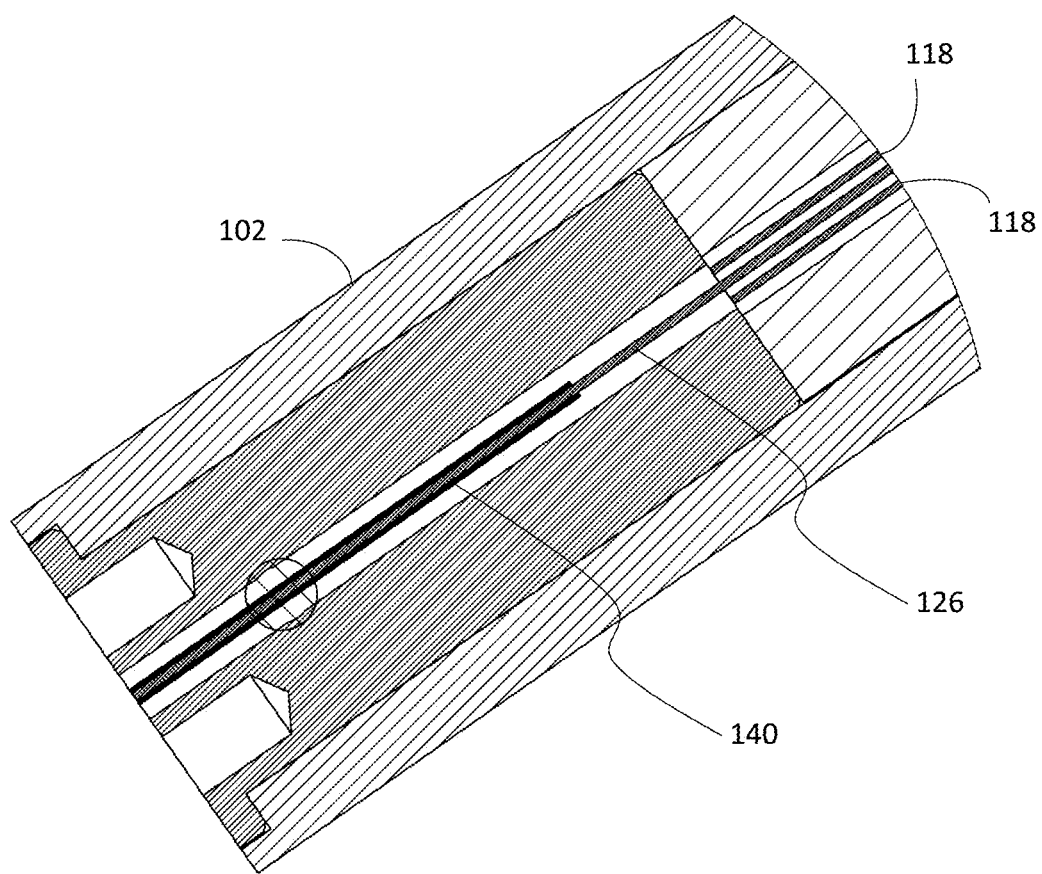
Figure 1I:
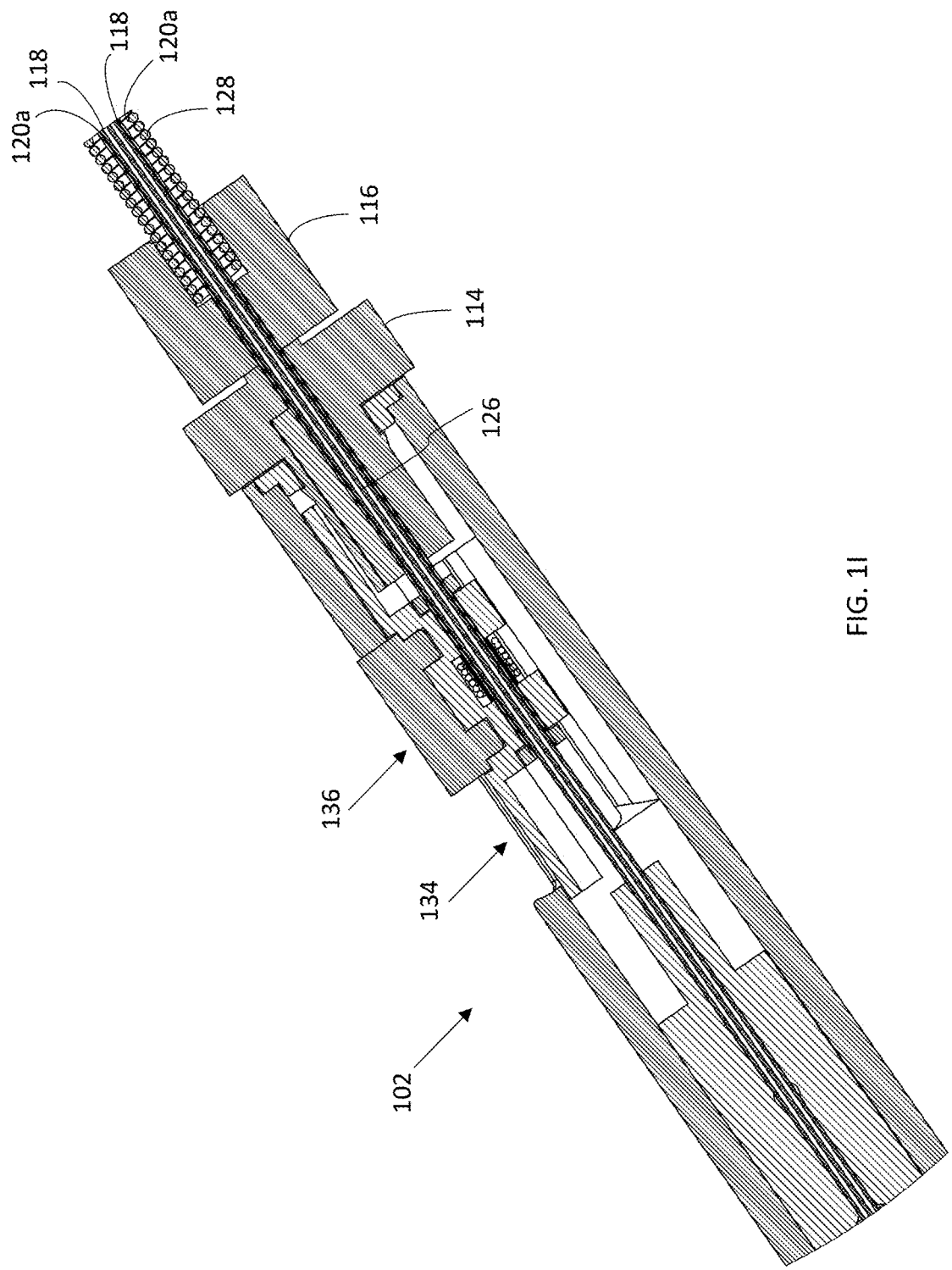

Referring to FIG. 1I, a posture adjustor, such as a second actuator 114, may be configured with handle 102 and used to align the orientation of patch 108 with the orientation of the perforated tympanic membrane. A middle sleeve actuator 120a, comprising a tube disposed between second actuator 114 at handle 102 and a proximal side of bend 106, may convey a rotational motion of actuator 114 to middle sleeve 120 over bend 106. In one implementation, stem 104 is provided with an inner spring 130 that mechanically connects middle sleeve actuator 120a to middle sleeve 120, to allow transferring an adjustment of the posture adjustor, such as a rotation of actuator 114, to a corresponding adjustment of the orientation of patch 108 over the bend 106.

It may be appreciated that other suitable mechanical elements structured to convey a rotational motion over a bend may be used.

A first activation of the deployment control 134, such as moving button 134 from a distal position to a middle position within niche 132, may cause a slight retraction of middle sleeve 120 relative to inner sleeve 118, such as may range from 3 to 7 millimeters (mm). This may cause the serrated distal end 120b of the middle sleeve 120 to withdraw proximally from patch 108, releasing the tension that the serrated end 120b of middle sleeve 120 applies to patch 108, thereby releasing patch 108 from the distal end of the middle sleeve 120. This release may allow the surgeon to position patch 108 in place, while evacuating the tip of middle sleeve 120 from the perforation, serving to enhance the visibility of the perforation by the surgeon.

Referring to FIG. 1H, a detailed cross-sectional view of the base of handle 102 is shown, illustrating a portion of the filament-based deployment system controllable by deployment control 134. Optionally, the actuation filament 126 is embedded within inner sleeve 118 of stem 104. Inner sleeve 118 may extend through to handle 102. Filament 126 may be anchored or secured to handle 102 at its proximal area, for example using glue 140 disposed around the proximal tip of filament 126, or using any other mechanical means. Filament 126 may be a biocompatible fiber-based thread, such as nylon thread, metallic wire, or other suitable material that allows attaching patch 108 to device and exert a tension to pull patch 108 proximally.

The filament-based deployment system may include an exposable distal end of the inner sleeve 118, such as a window of a side cutout in its wall, along a length denoted 118a. Responsive to a rotation or sliding motion of middle sleeve 120 causing inner sleeve 118 to no longer be encased by middle sleeve 120, the inside of inner sleeve 118 may be exposed at exposable distal end 118a.

Patch 108, also shown in FIGS. 6A-6C from various angles, is optionally composed of a disc 136 and a securing mechanism 138. In the embodiment shown in the figures, securing mechanism 138 is a proximally positioned cord 138b threaded through a hole, optionally central, in disc 136; the cord may have a wider distal end 138a that secures it from a distal side of the disc, and a bulgy proximal end 138c. Disc 136 may have a diameter of 3 to 10 millimeters, and a thickness of 0.1 to 1 millimeters, as one example. Cord 138b may be between 5 to 50 millimeters long, as one example.

Optionally, patch 108 is constructed from a resilient material that flexes to fit through the perforation, and restores its original shape when emerging in the middle ear at the internal side of the tympanic membrane.

Reference is now made to FIG. 1F which shows a cross section of the distal tip of stem 104. Patch 108 may be secured at a distal end of stem 104 as follows: Cord 138b may extend from the distal end of the middle sleeve 120 to the exposable distal end 118a of the inner sleeve 118 where it engages with actuation filament 126. Actuation filament 126 may have a bulgy distal end 126a. The engagement may be implemented by positioning bulge 138c of cord 138b proximal to bulge 126a of filament 126. When middle sleeve 120 covers exposable distal end 118a, bulgy distal end 138c of cord 138b is prevented from sliding over bulge 126a of actuation filament 126, securing bulgy distal end 138c at sleeve section 118a. Thus, when middle sleeve 120 encases the exposable distal end 118a of inner sleeve 118, patch 108 is affixed at the distal end of the middle sleeve 120.

A second activation of the deployment control 134, such as moving button 134 from a middle position to a proximal position within niche 132, may cause middle sleeve 120 to withdraw proximally with respect to the inner sleeve 118 and expose the exposable distal end 118a, allowing bulge 138c to slide distally over bulge 126a and exit the inner sleeve through its distal end. This disengages cord 138b from actuation filament 126 and release patch 108 from the tympanoplatic patch applicator 100.

Optionally, the deployment control is provided with a safety mechanism configured to prevent an accidental second activation of the deployment control. The safety mechanism may be implemented as a stopper, such as a small protrusion or step within niche 132 that requires moving button 134 sideways before moving from the middle to the proximal positions.

Figures 2A, 2B, 2C:
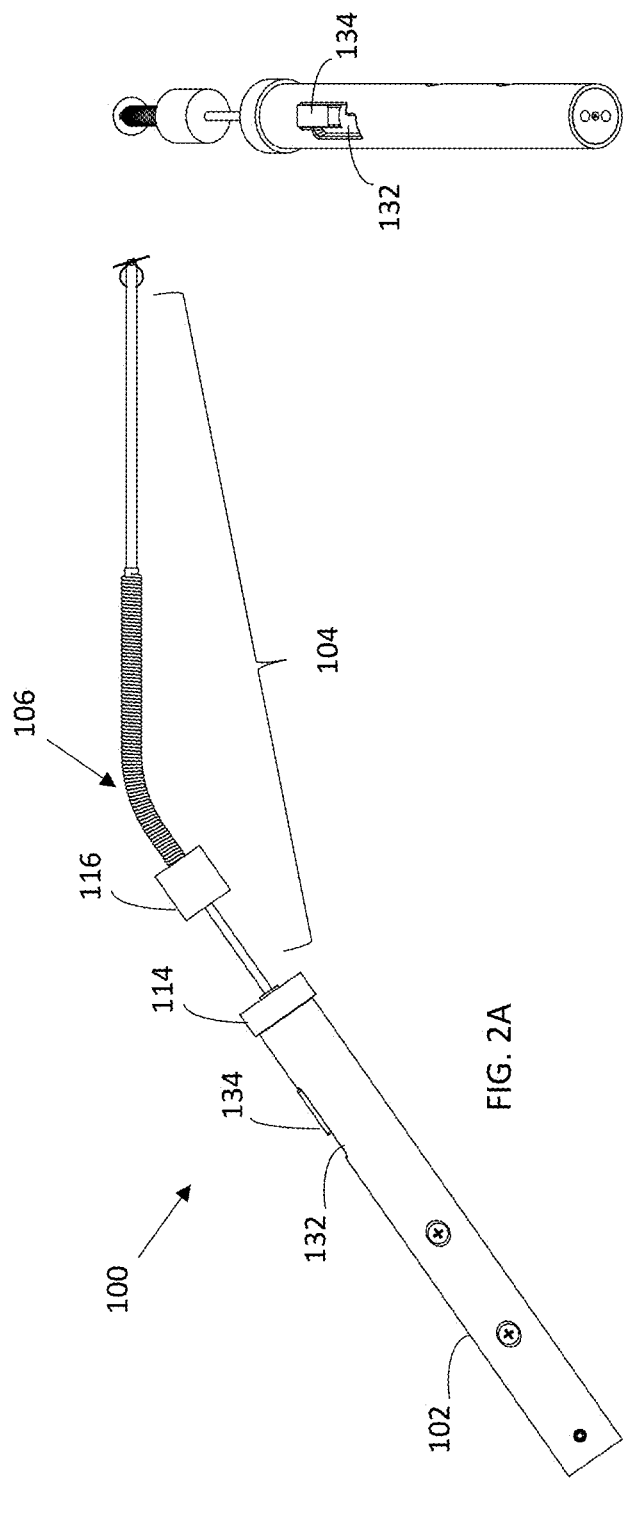
FIGS. 2A-2F show various views of the tympanoplatic patch applicator of FIGS. 1A-1I in an initial deployment stage, in accordance with an embodiment.
Figure 2D:
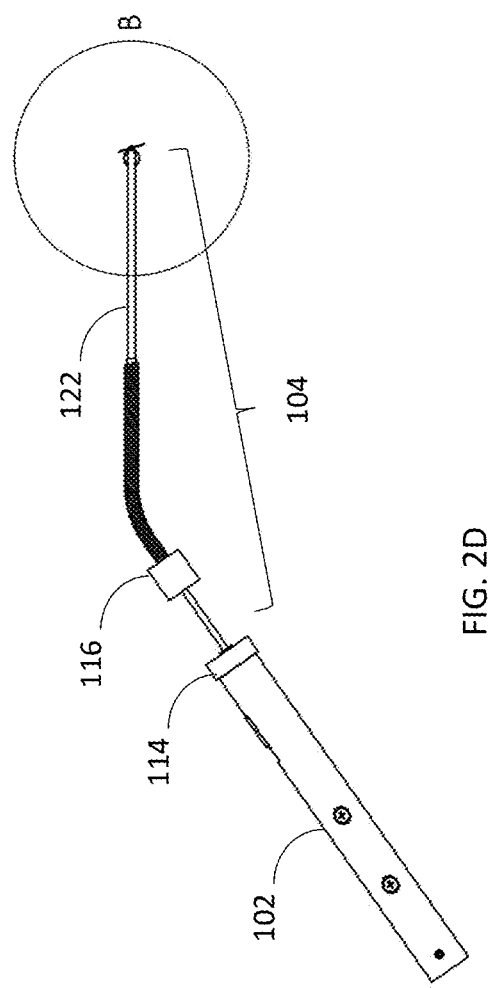
Figure 2E:
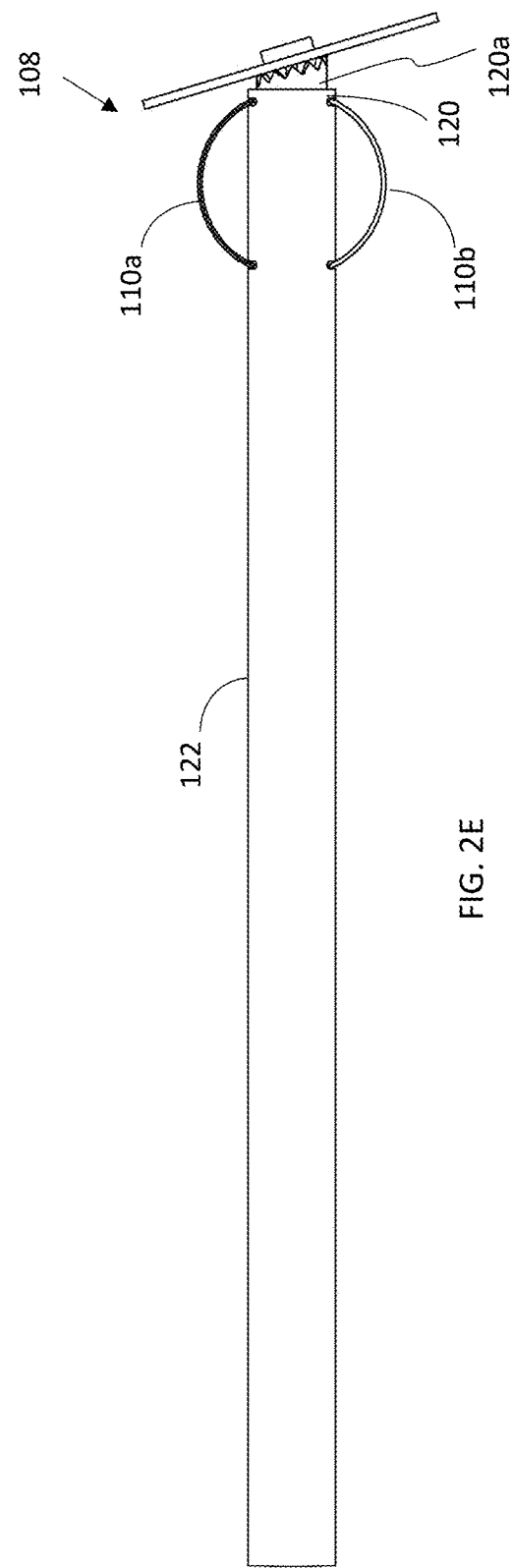
Figure 2F:
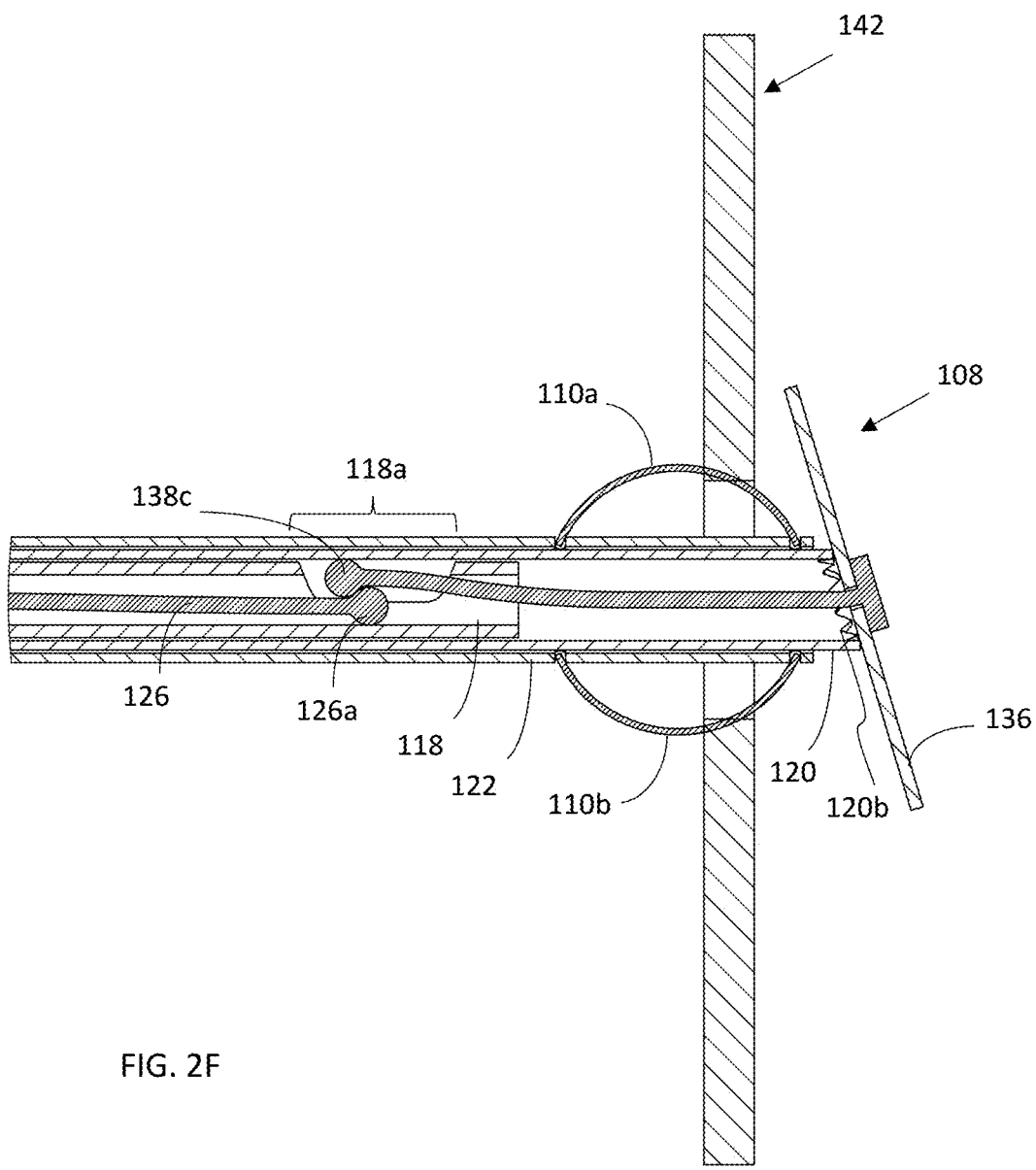

Reference is now made to FIGS. 2D-2F which illustrate a debridement mechanism of applicator 100, in accordance with an embodiment. FIG. 2D shows a side view of applicator 100; FIG. 2E shows a detailed view of section B of FIG. 2D; and FIG. 2E shows a detailed cross-sectional view of blades 110a-b penetrating perforation 142a of the tympanic membrane 142. The debridement mechanism may include outer sleeve 122, outer sleeve actuator 116 disposed with handle 102, and at least one protruding blade 110 disposed at a distal end of the outer surface of outer sleeve 122. Optionally, the at least one protruding blade 110 is implemented by two protruding, curved blades 110a-b. The curvature of blades 110a-b may control a penetration depth of the blades 110a-b into the perforation.

Outer sleeve actuator 116 may be a tube disposed between handle 102 and a proximal side of bend 106, and may control the advancement and retraction of outer sleeve 122 to and from the distal end of stem 104, thereby controlling the debridement mechanism. Optionally, actuator 116 may convey motion to the outer sleeve 122 over bend 106, such as via an outer spring 128, as shown in FIG. 1G, or other suitable mechanical element structured to convey motion over a bend. Outer spring 128 may be disposed on stem 104 and may mechanically connect actuator 116 to outer sleeve 122 via a connecting ring 124. Spring 128 may transfer a motion, such as an advancement, retraction, or rotation of the debridement actuator 116 to outer sleeve 122 over the bend 106 of deployment stem 104, thereby enabling the advancement and retraction of the outer sleeve 122 relative to the middle sleeve 120 over the bend 106. This allows actuator 116 to control the debridement mechanism over bend 106.

Referring to FIG. 2D, advancing actuator 116 distally away from actuator 114 at the proximal base of stem 104 may advance outer sleeve relative 122 to the middle sleeve 120 until blade(s) 110a-b reach the distal end of the deployment stem 104, as shown in FIG. 2E, until blades 110a-b and come into contact with the circumference of the perforation, as illustrated in FIG. 2F. Rotating actuator 116 may rotate outer sleeve 122 relative to the middle sleeve 120, thereby rotating the protruding blade(s) 110a-b and causing a debridement of the circumference of the perforation. Retracting actuator 116 may retract outer sleeve 122 relative to the middle sleeve 120, retracting blades 110a-b once the debridement has been completed.

Optionally, the debridement mechanism further comprises a niche for collecting debrided tissue. For example, the area delimited between the curvature of at least one of blades 110a-b and the outer surface of outer sleeve 122 may form the niche where debrided tissue may collect during the debridement, preventing this tissue from falling into the middle ear.

Optionally, the debridement mechanism includes a penetration depth controlling mechanism that limits the penetration depth of blades 110a-b by limiting the advancement of outer sleeve 122 relative to the middle sleeve 120. For example, the penetration depth controlling mechanism may be implemented by ring 150, shown in FIG. 1G. Ring 150 may block the distal extension of outer sleeve 122 by engaging with the inner surface of actuator 116 as actuator 116 is pushed distally, preventing blades 110a-b from penetrating too deeply into the perforation and thereby preventing any further damage to the tympanic membrane by blades 110a-b. For example, ring 150 may prevent outer sleeve 122 from extending distally beyond middle sleeve 120.

The following steps describe a method for deploying a tympanoplatic patch at the internal side of a perforated tympanic membrane using applicator 100:

Step 1: Referring to FIGS. 1A-1F, when actuator 116 is positioned flush with actuator 114 at the distal end of handle 102, outer sleeve 122 is retracted, exposing middle sleeve 120 with patch 108 affixed to serrated distal end 120b, and comprising the distal end of distally disposed stem 104 of applicator 100. Thus exposed, patch 108 may be introduced into a patient's ear canal by inserting the distal end of stem 104 into the ear canal.

Step 2: The distal end of stem 104 may be progressed therein until patch 108 penetrates through the perforation 142a in the tympanic membrane 142. Patch 108, constructed from a resilient material, flexes to fit through the perforation and restores its original disc shape when emerging in the middle ear, at the distal side of the tympanic membrane.

The deployment control, provided with proximally disposed handle 102 of applicator 100, may be used to maneuver the filament-based deployment system that releases patch 108 from the distal end of stem 104 at the internal side of the tympanic membrane, and the patch may be deployed on the internal side of the perforated tympanic membrane, as follows:

Step 3: If needed, while patch 108 is positioned at the internal side of the tympanic membrane, the posture of patch 108 may be adjusted to align the orientation of patch 108 with the orientation of the perforated tympanic membrane 142 by using a posture adjustor, implemented by second actuator 114 provided with proximally disposed handle 102. Rotating the posture adjustor 114 rotates middle sleeve 120 of applicator 100 through a rotation of inner spring 130. Since patch 108 is secured to beveled and serrated distal end 120b of the middle sleeve 120, rotating sleeve 120 adjusts the posture of patch 108, accordingly.

Reference is not made to FIGS. 2A-2F, which show various views of the tympanoplatic patch applicator of FIGS. 1A-1I in an initial deployment stage, in accordance with an embodiment. FIGS. 2A-2F show a debridement mechanism that may be activated to debride dead tissue from the circumference of perforation 142a. As a result, the circumference of the debrided perforation may be wetted with fresh blood released by the debriding. The debridement may be activated, as follows:

Step 4: To activate the debridement mechanism, debriding actuator 116, disposed with the proximally disposed handle 102 of applicator 100, may be used to advance at least one debridement blade, such as blades 110a-b, to the distal end of stem 104, as follows: outer sleeve 122 may be advanced distally by grasping and pushing actuator 116, positioned at the proximal base of stem 104, distally. As shown in FIGS. 1G and 1I, actuator 116 is attached to outer spring 128 which is, in turn, attached to outer sleeve 122 via a ring 124. Thus, pushing first actuator 116 distally away from actuator 114 causes outer spring 128 to be pushed distally, which causes outer sleeve 122 disposed with blades 110a-b to be extended distally, and encase the distal end of middle sleeve 122. This positions blades 110a-b flush with the distal end of stem 104 for debridement of the tympanic membrane.

Step 5: Positioned thus, rotating first actuator 116 rotates outer sleeve 122 which rotates blades 110a-b about the circumference of the perforation 142a, causing a debridement of the perforated tympanic membrane 142.

Step 6: The removed tissue may be collected in a niche of applicator 100, formed between curved blades 110a-b and sleeve 122, preventing the removed tissue from reaching the middle ear.

Reference is now made to FIGS. 3A-3F which show various views of the tympanoplatic patch applicator of FIGS. 1A-1I in a follow-up deployment stage, in accordance with an embodiment.

Figure 3C:
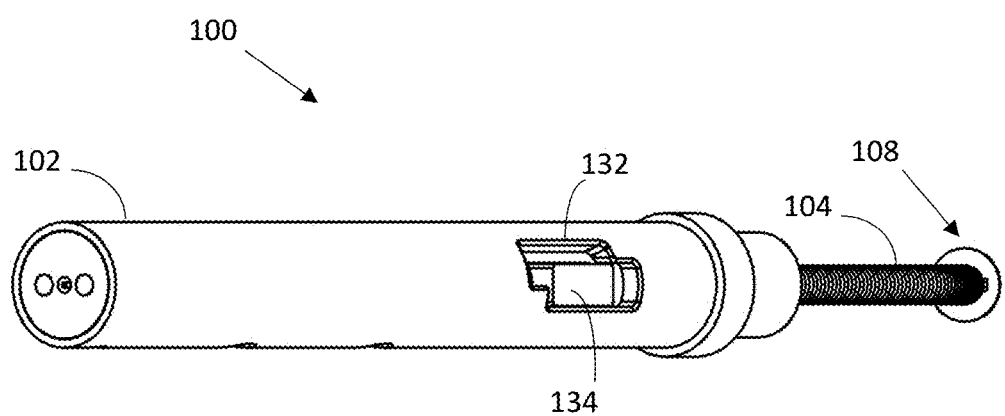

Step 7: Referring to FIGS. 3A-3C, the at least one blade 110a-b may be removed from the perforation by using the debridement actuator 116 to retract the at least one blade from the distal end of the applicator 100, as follows: outer sleeve 122 may be retracted by pulling actuator 116 proximally towards actuator 114 causing outer sleeve 122 to retract, removing blades 110a-b from perforation 142a. This is illustrated in the contrast between FIG. 2A, which shows actuator 116 positioned distally from actuator 114 with a gap therebetween, and resulting in the advancement of outer sleeve 122, versus FIG. 3A, which shown actuator 116 flush with actuator 114 at the proximal base of stem 104, and resulting in the retraction of outer sleeve 122.

Figure 3D:
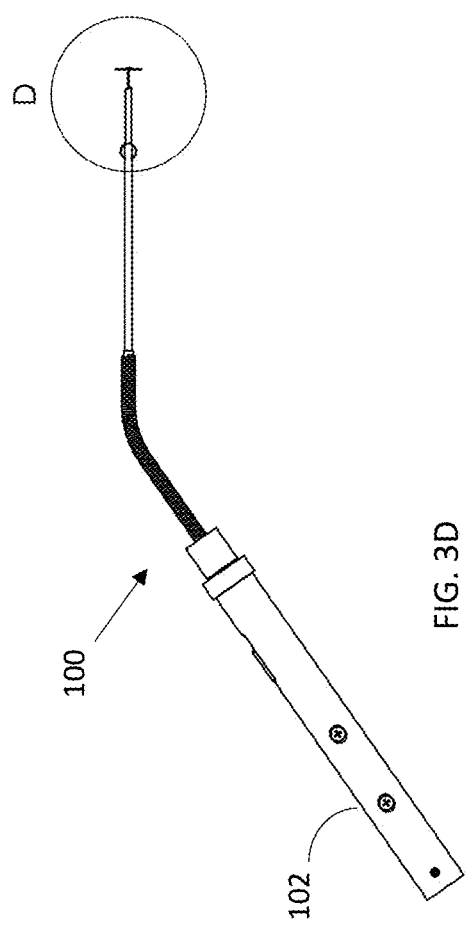
Figure 3E:
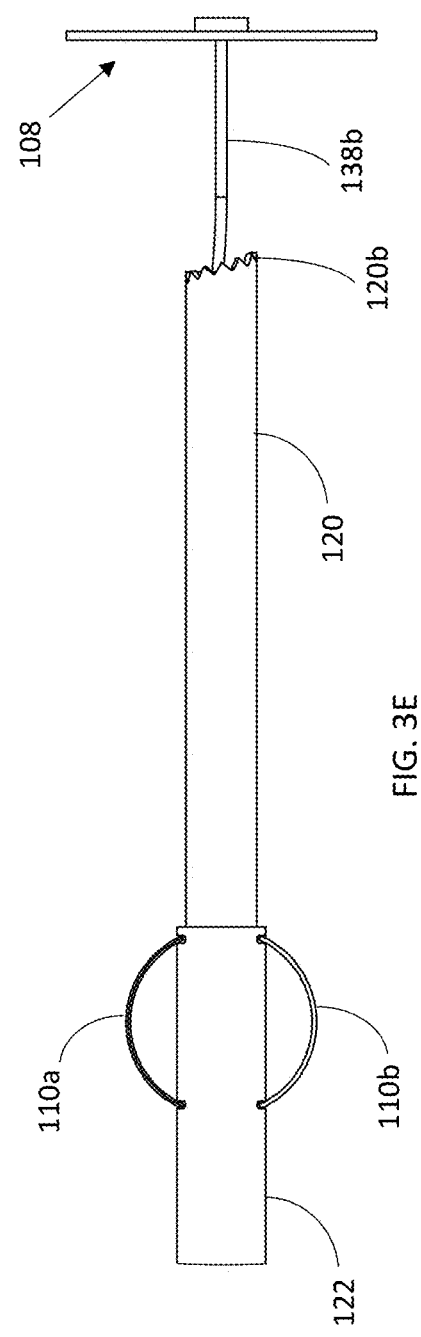

Additionally, the deployment control, comprising button 134 and niche 132, may be used to maneuver the filament-based deployment system and detach patch 108 from serrated distal tip 120b of stem 104 in a first detachment stage, as follows:

Step 8: Referring to FIGS. 3A-3F, button 134 may be moved from the distal position in niche 132, as shown in FIGS. 1A-1C, to the middle position in niche 132, as shown in FIGS. 3A-3C, causing serrated tip 120b of middle sleeve 120 to detach from patch 108 and release the applied tension, thus leaving patch 108 attached to applicator 100 only by the engagement of cord 138b with filament 126. FIG. 3E, which is a detailed view of section D of FIG. 3D, shows patch 108 in the first stage of detachment from applicator 100.

Figure 3F:
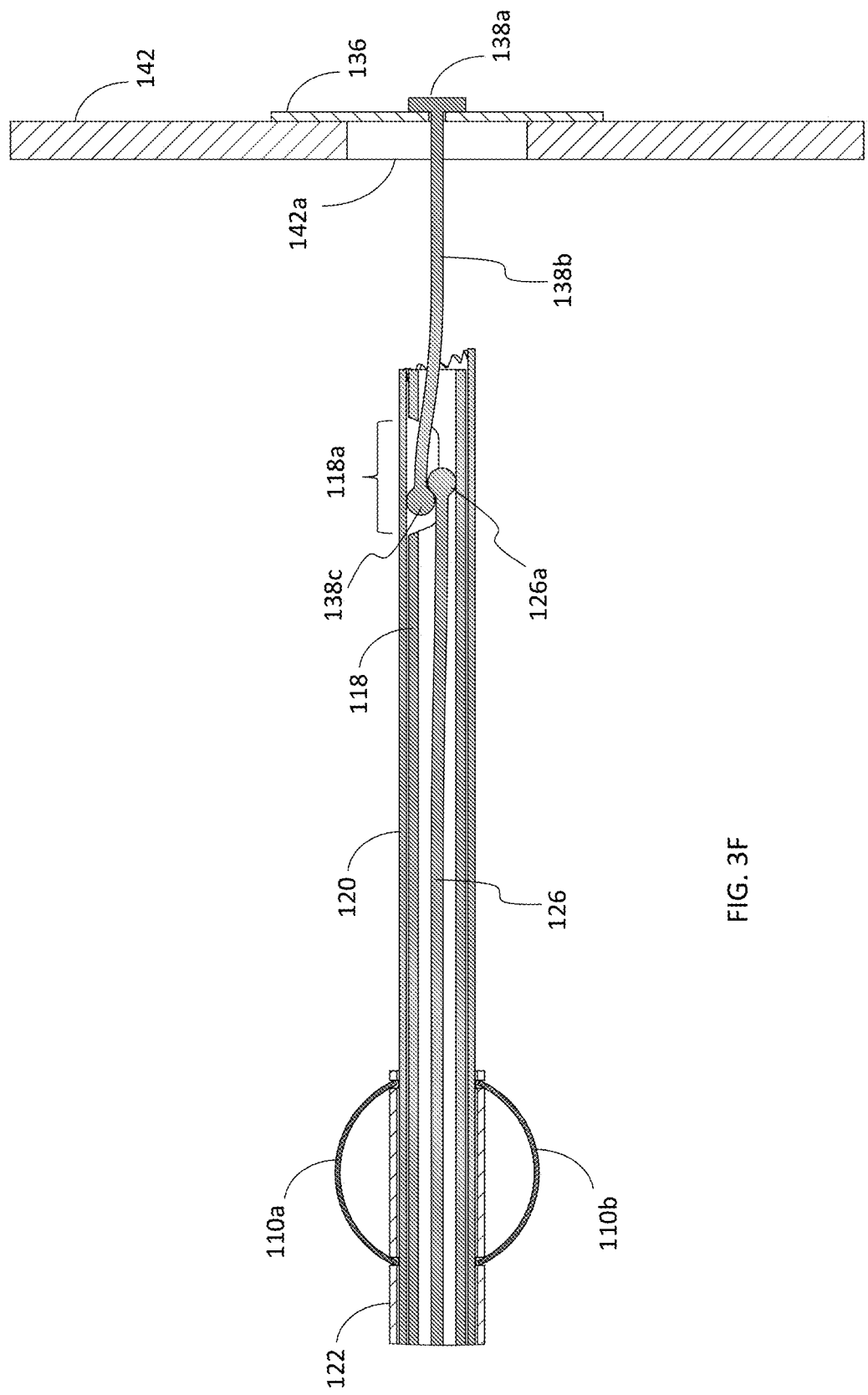

Step 9: Referring to FIG. 3F, the deployment of patch 108 may continue by pulling the entire applicator 100 proximally, causing inner sleeve 118 to be retracted proximally. This proximal motion causes patch 108 to be pulled proximally until it comes into contact with the internal side of the tympanic membrane 142. Patch 108 may then be secured to the tympanic membrane using the fresh blood, released by the debridement, as a glue. inner sleeve 118 may then be retracted by pulling applicator 100 proximally.

Figure 4C:
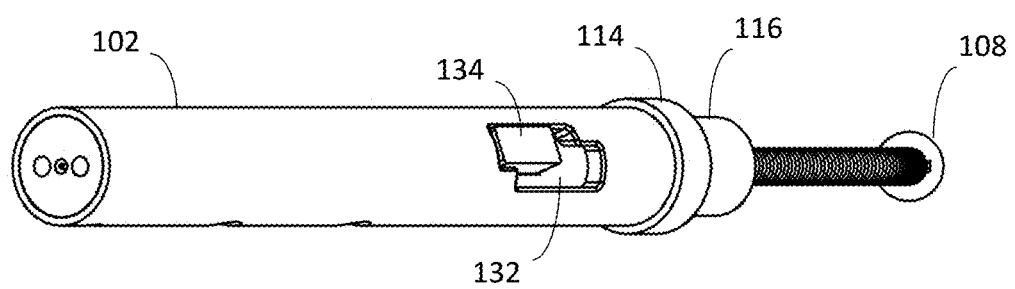
Figure 4D:
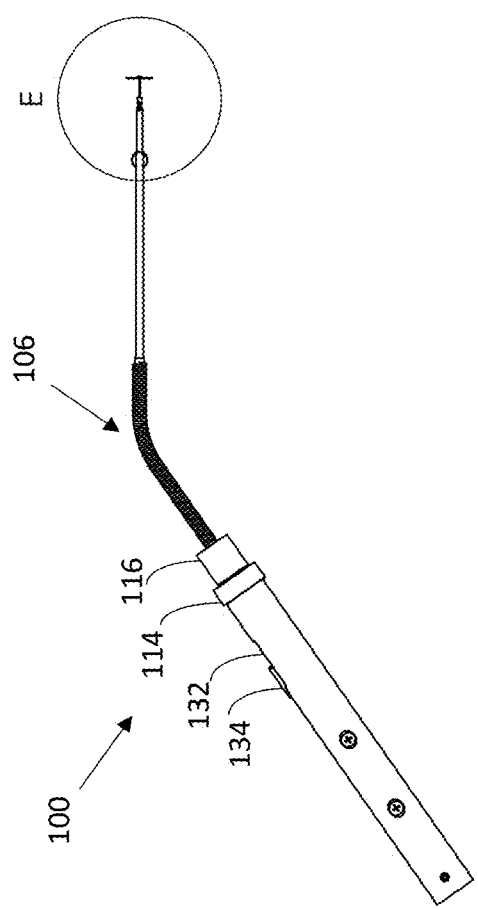
Figure 4E:
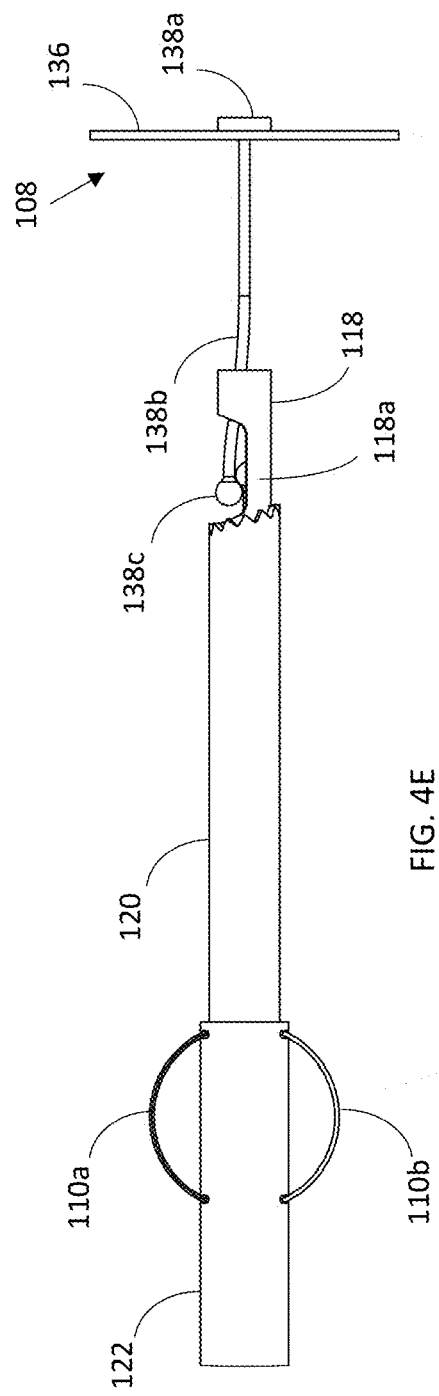
Figure 4F:
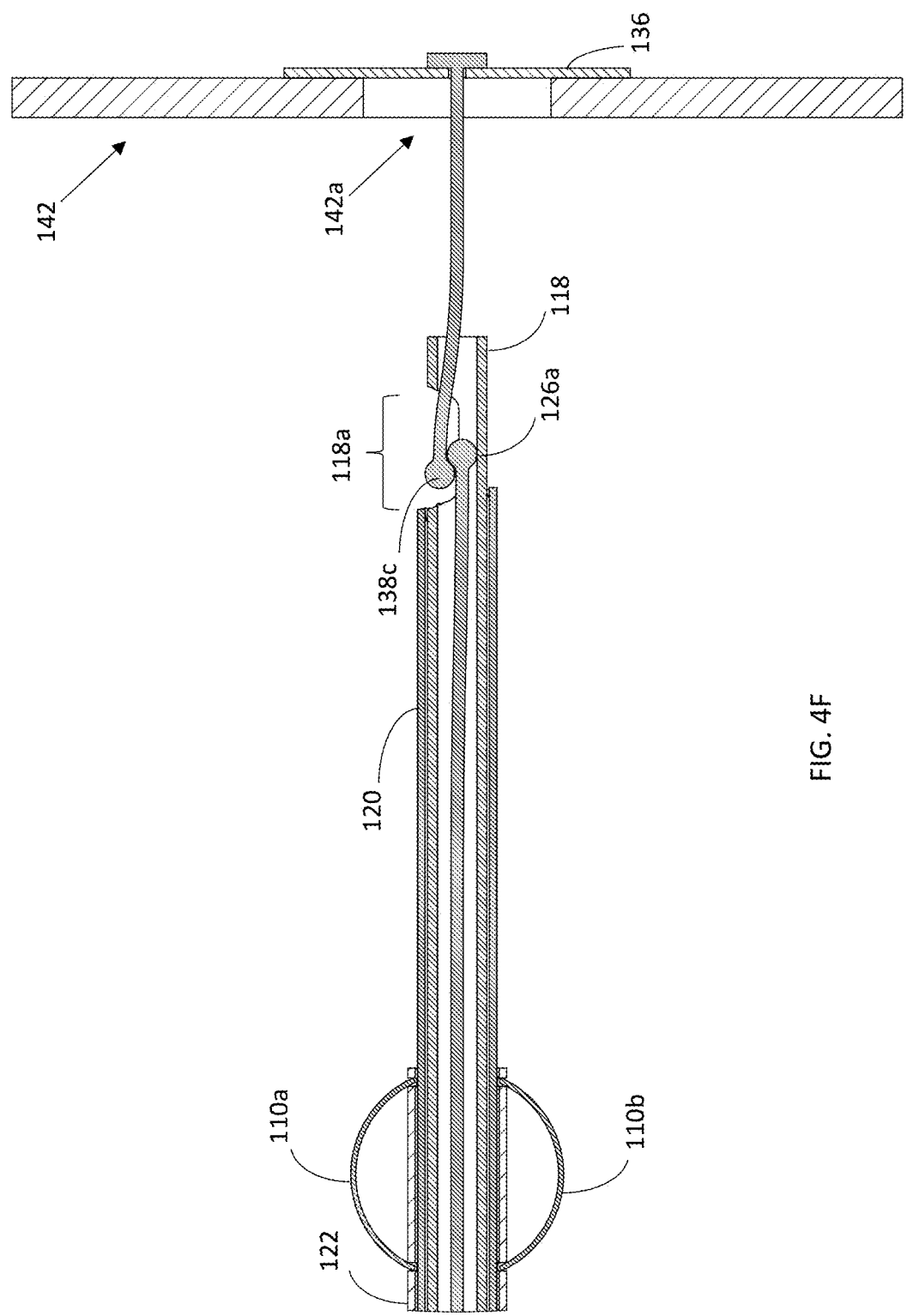

Reference is now made to FIGS. 4A-4F which show various views of the tympanoplatic patch applicator of FIGS. 1A-1I in a follow-up deployment stage, in accordance with an embodiment. The deployment control may be used to maneuver the filament-based deployment system to decouple cord 138b of patch 108 from filament 126 of applicator 100, in a second detachment stage:

Step 10: Referring to FIGS. 4A-4F, button 134 may be moved from the middle position in niche 132, as shown in FIGS. 3A-3C, to the proximal position in niche 132, as shown in FIGS. 4A-4C, causing middle sleeve 120 to withdraw proximally with respect to the inner sleeve 118 and expose the exposable distal end 118a, allowing bulge 138c to slide distally over bulge 126a and exit the inner sleeve through its distal end. This disengages cord 138b from actuation filament 126 and releases patch 108 from the tympanoplatic patch applicator 100, comprising the second detachment stage. As can be seen in FIG. 1I, inner spring 130, mechanically connects middle sleeve actuator 120a to middle sleeve 120, and button 134 is mechanically connected to middle sleeve actuator 120a within handle 102, thus a proximal motion by button 134 may cause a corresponding proximal motion of middle sleeve actuator 120a, retracting middle sleeve 120 with respect to inner sleeve 118, accordingly. This exposes distal end 118a, allowing cord 138b to disengage from filament 126.

Figure 5A:
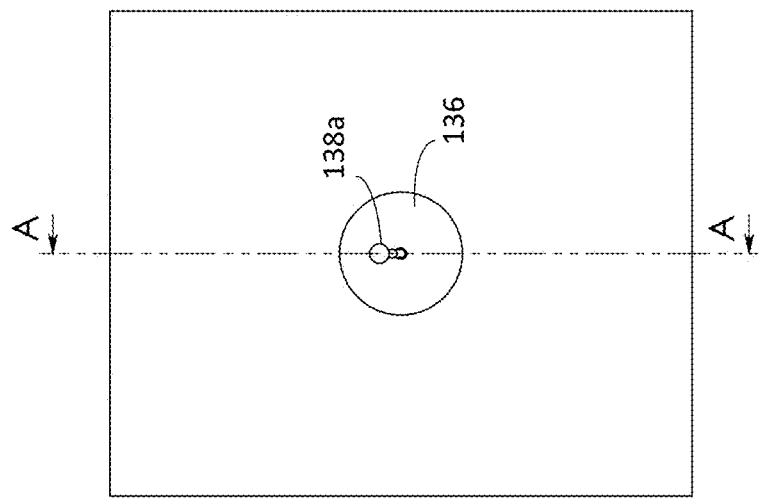
FIGS. 5A-5C show various views of a deployed tympanoplatic patch, in accordance with an embodiment.
Figure 5B:
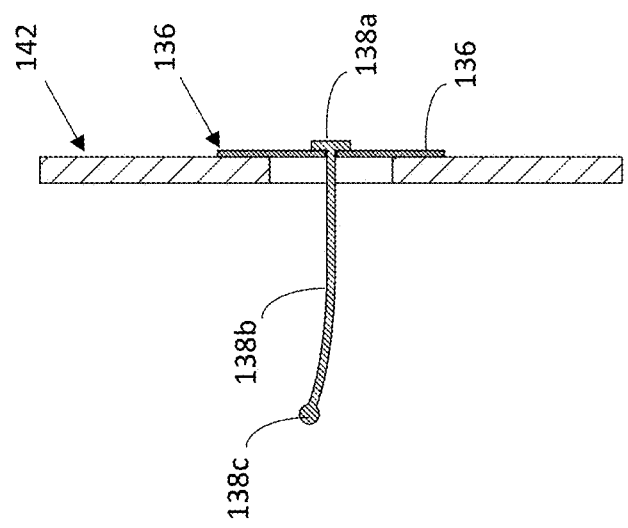
Figure 5C:
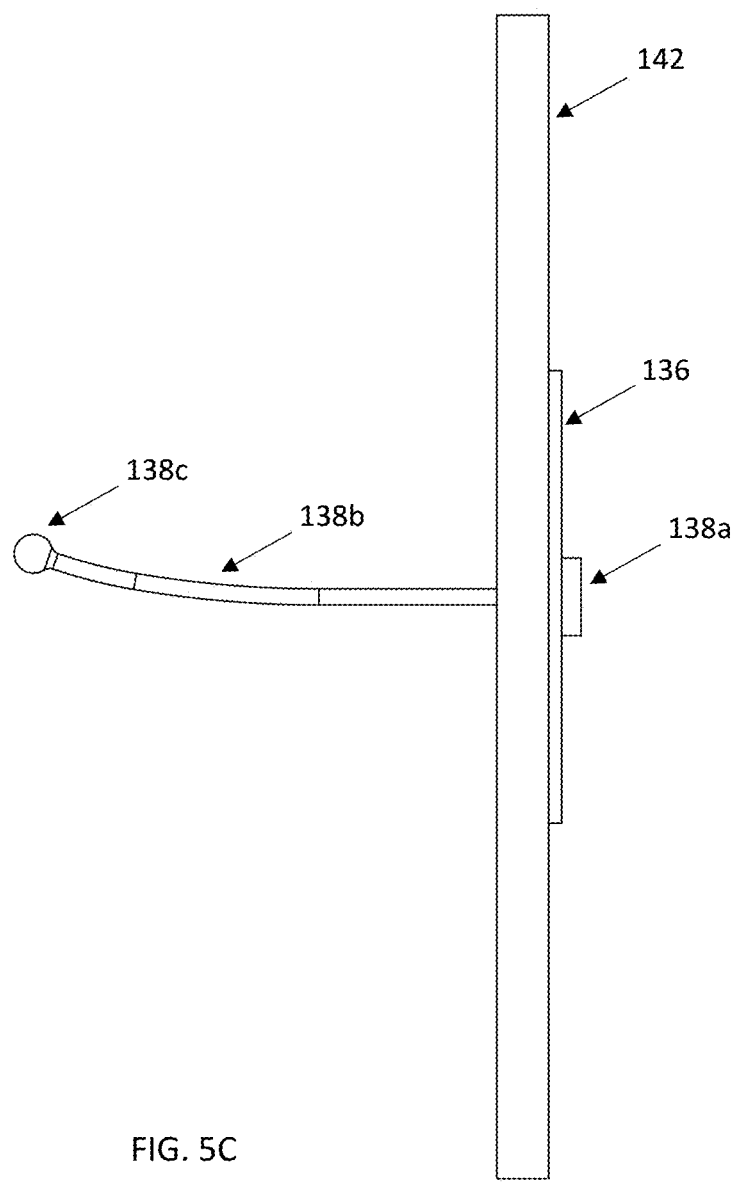

Reference is now made to FIGS. 5A-5C which, taken together, show patch 108 after it has been released from applicator 100. Fresh blood (not shown) released as a result of the debridement of the perforation may serve to secure patch 108 in place, attached to the inner side of the tympanic membrane and covering the perforation. Optionally, the surgeon may wait several minutes prior to releasing patch 108 from applicator 100, to enable the blood to at least partially coagulate and essentially glue the patch to the inner side of the tympanic membrane. Alternatively, biological glue may be injected to the interface between patch 108 and the inner side of the tympanic membrane before contact between the two is made. This may be performed using an injection channel in stem 104 (not shown).

Following the above procedure, and over a typical period of several weeks, new cells may grow at the circumference of the perforation, slowly closing the perforation. The proximal side of patch 108 may serve as a bedding for this cellular growth. Patch 108 may eventually degrade leaving a fully, repaired tympanic membrane without any external remnants.

Reference is now made to FIGS. 7A-7F, which show multiple exemplary embodiments of a tympanic patch, such as any of patches 108, and 808P and 808D described below.

The present invention discloses, in one embodiment, a biodegradable patch construct having a first thickness and a second thickness. Optionally, disclosed herein a unitary biodegradable patch construct having a first thickness and a second thickness. Optionally, a biodegradable patch comprises hydrogel. Optionally, a biodegradable patch consists a hydrogel or a combination of hydrogels.

"hydrogel", in some embodiments, is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, temperature change, pH change or cross-linking. The hydrogels employed in this invention rapidly solidify to keep the cells evenly suspended within a mold until the gel solidifies. The hydrogels are also biocompatible, e.g., not toxic, to cells, e.g., cells suspended in the hydrogel, or in the surrounding membrane.

Any hydrogel composition known to one skilled in the art is encompassed within the invention, e.g., any of the hydrogel compositions disclosed in the following reviews: Graham, 1998, Med. Device Technol. 9(1): 18-22; Peppas et al, 2000, Eur. J. Pharm. Biopharm. 50(1): 27-46; Nguyen et al, 2002, Biomaterials, 23(22): 4307-14; Heninel et al, 2002, Adv. Drug Deliv. Rev 54(1): 13-36; Skelhorne et al, 2002, Med. Device. Technol. 13(9): 19-23; Schmedlen et al, 2002, Biomaterials 23: 4325-32; all of which are incorporated herein by reference in their entirety.

Optionally, the patch comprises biodegradable and biocompatible polymers. Optionally, a biodegradable polymer and/or biocompatible polymer is a hydrogel. Optionally, the biodegradable and biocompatible polymers based patch comprises: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), sulfonated polymers, or any combination thereof. Optionally, the biodegradable biocompatible patch comprises: alginate, chitosan, pluronic, collagen, agarose, gelatin, cellulose or any combination thereof. Optionally, the biodegradable biocompatible patch comprises of chemical and physical modifications of these polymers.

A "hydrogel-cell composition" is a suspension of a hydrogel comprising cells. These cells can be isolated directly from a tissue source or can be obtained from a cell culture. A "tissue" is a collection or aggregation of particular cells embedded within its natural matrix, wherein the natural matrix is produced by the particular living cells.

Optionally, a suitable polymer hydrogel according to the invention is one that is biologically compatible and non-cytotoxic. Optionally, a suitable polymer hydrogel according to the invention is one that is formed through controllable crosslinking (gelation). Optionally, a suitable polymer hydrogel according to the invention is one that is compatible with viability of cells suspended in a solution.

Optionally, provided herein a biodegradable patch construct ("patch" or "construct") having a first thickness and a second thickness. Optionally, provided herein a biodegradable patch comprising an upper portion and a bottom portion. In some embodiment, a portion as used herein is synonymous with "surface".

Optionally, the second thickness is from 1.2 to 100 times thicker than said first thickness. Optionally, the second thickness is from 1.2 to 50 times thicker than said first thickness. Optionally, the second thickness is from 5 to 60 times thicker than said first thickness. Optionally, the second thickness is from 3 to 25 times thicker than said first thickness.

Optionally, the second thickness is a result of a projection from the upper portion. Optionally, the second thickness is a result of a projection from the bottom portion. Optionally, the second thickness is a result of projections from both the upper and bottom portions (see the crossed lines in the patch of FIG. 7E). Optionally, the second thickness results from thickening of a segment of the upper portion, the bottom portion, or both. Optionally, the second thickness provides structural support for the patch. Optionally, the second thickness enables the patch be present in a folded position and in an open position (as further described herein). Optionally, the second thickness renders the patch fully open by default. Optionally, a patch as described herein is in an open configuration unless it is attached or contained within a patch-tympanic membrane insertion device. Optionally, a patch as described herein is in an open configuration unless it is associated with a patch-tympanic membrane insertion device. Optionally, the bottom portion is portion which is adapted or configured to face the tympanic membrane. Optionally, the bottom portion is the tympanic membrane portion of the patch.

Figure 7A:
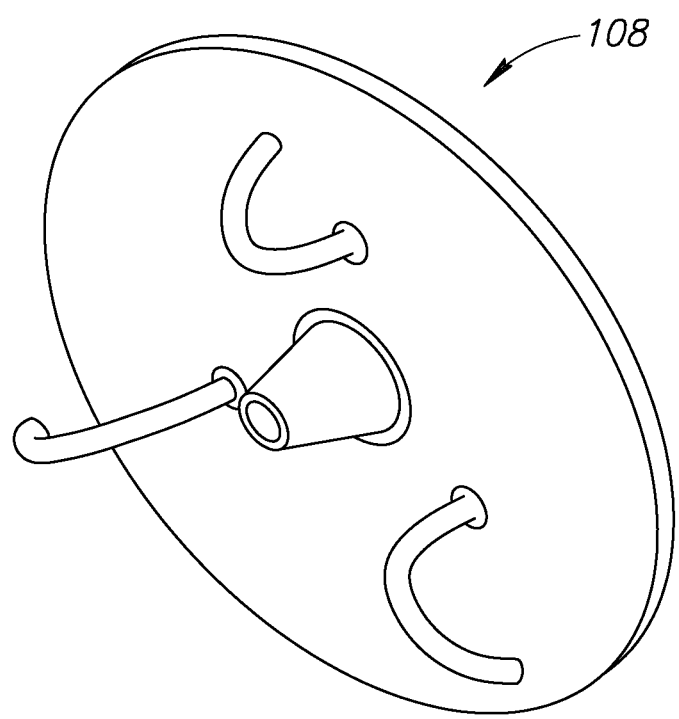
FIGS. 7A-7F show multiple exemplary embodiments of a tympanic patch.
Figure 7B:
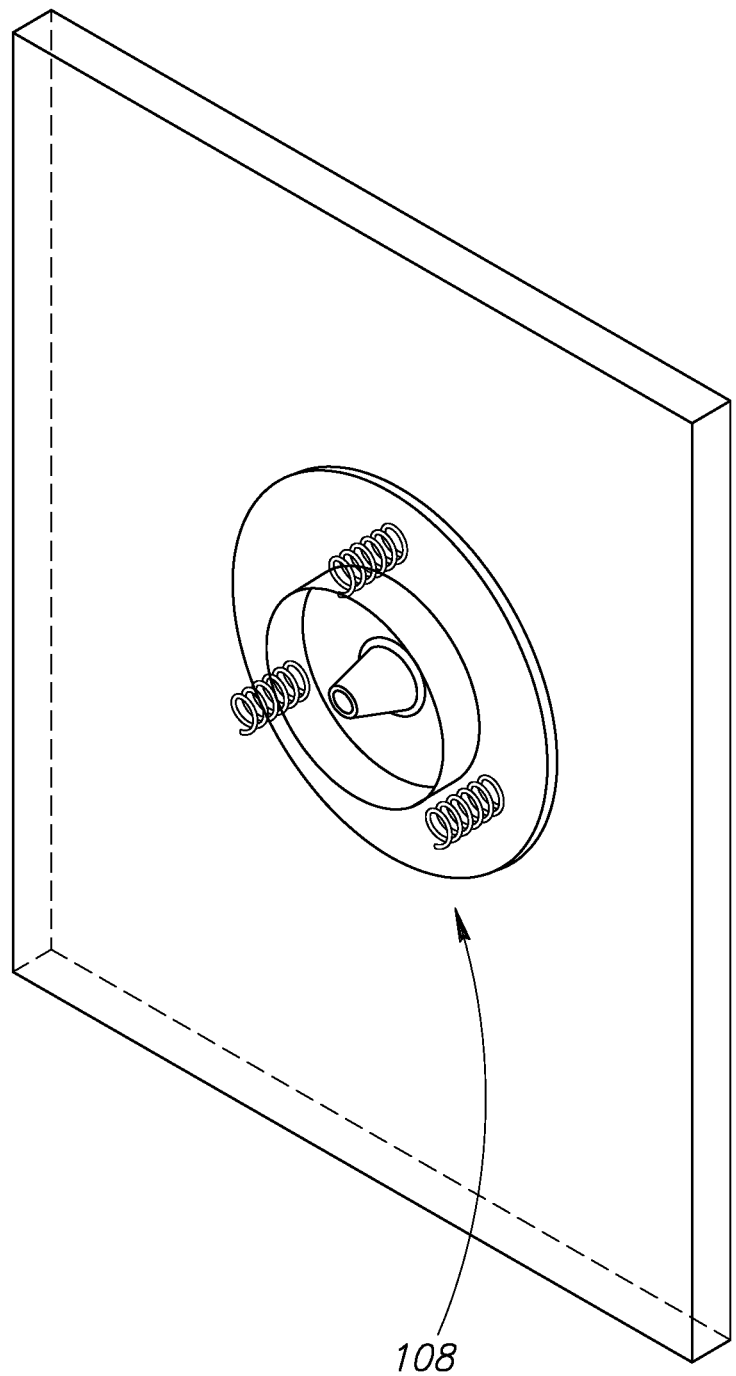
Figure 7C:
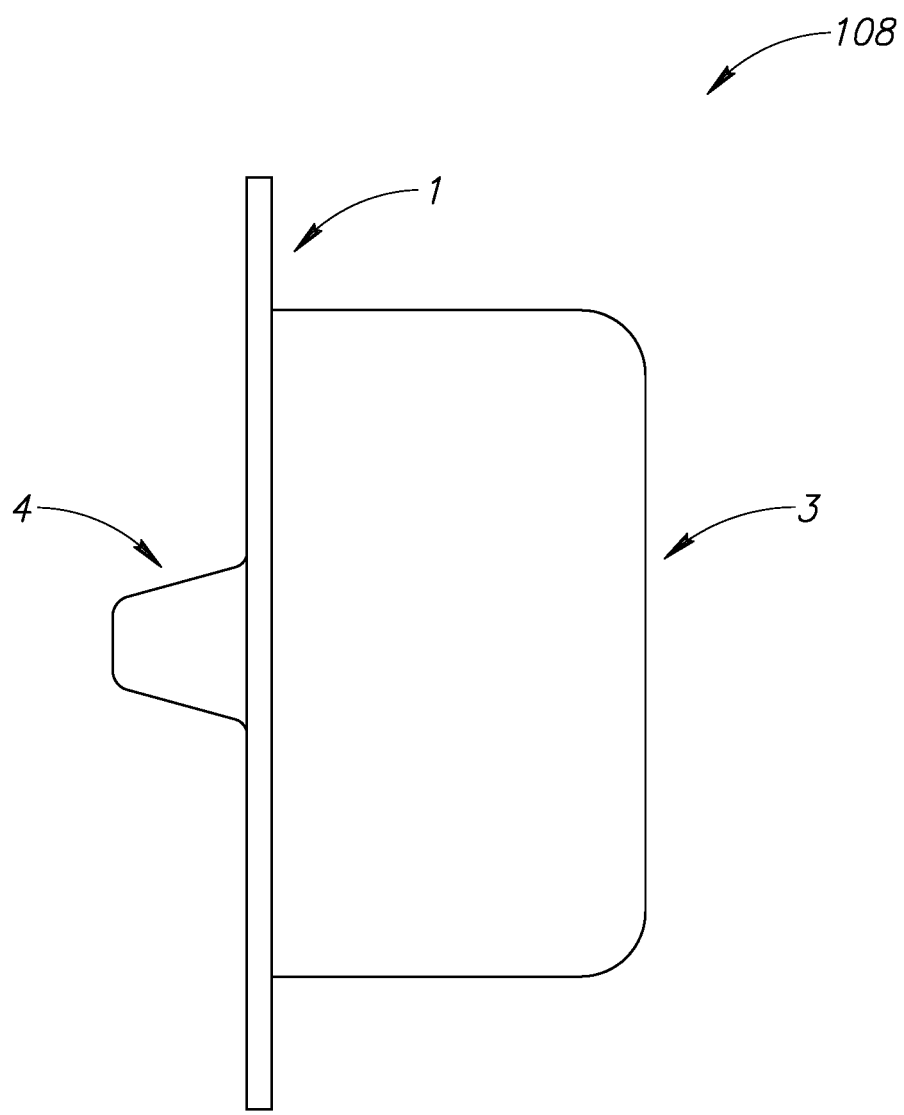

Optionally, a patch of the invention comprises a second thickness in the form of at least one projection such as element 3 in FIG. 7C. Optionally, a patch of the invention comprises a second thickness in the form of at least one projection such as element 4 in FIG. 7C. Optionally, a patch of the invention comprises a second thickness in the form of at least one projection such as element 3 in FIG. 7C and at least one projection such as element 4 in FIG. 7C. Optionally, a patch of the invention comprises a first thickness such as element 1 in FIG. 7C.

Figure 7D:
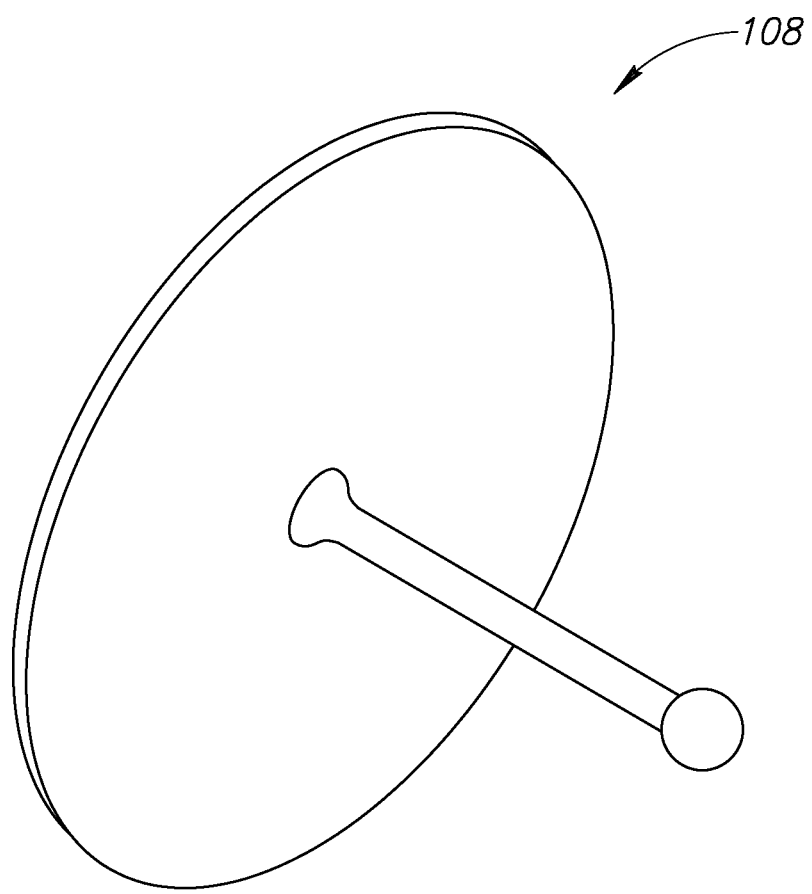
Figure 7E:
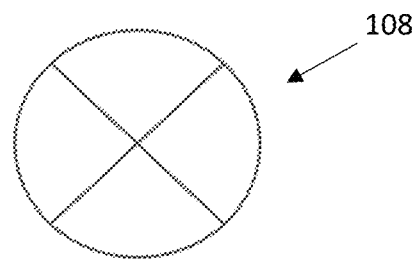
Figure 7F:
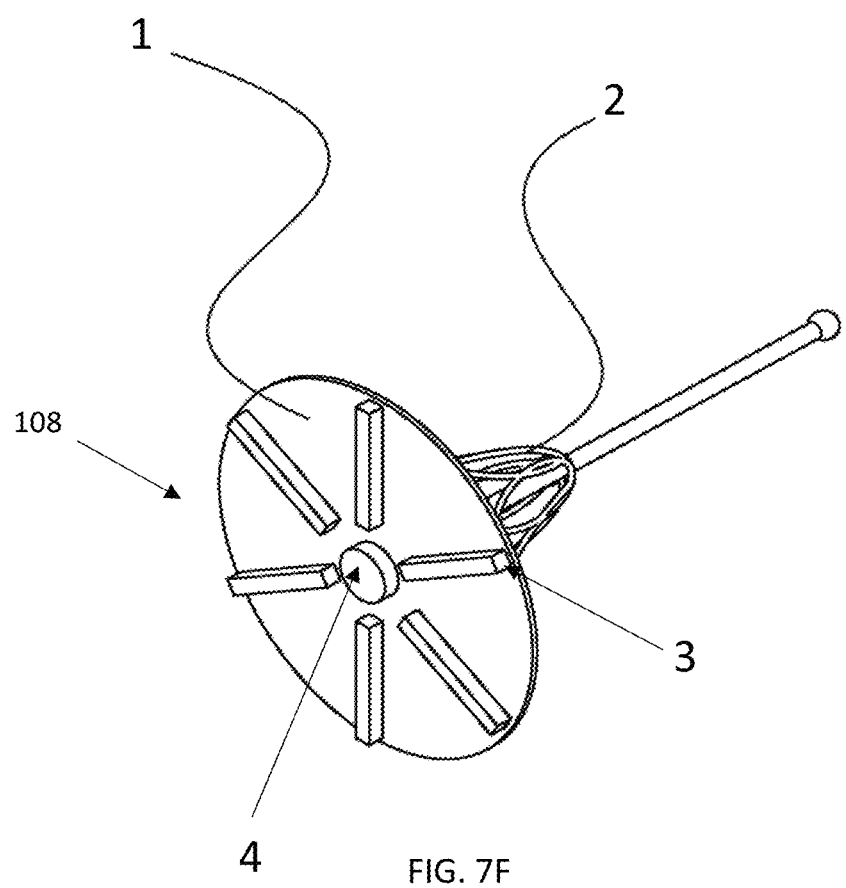

Optionally, a patch of the invention comprises a second thickness in the form of at least one projection such as element 3 in FIG. 7F. Optionally, a patch of the invention comprises a second thickness in the form of at least one projection such as element 4 in FIG. 7F. Optionally, a patch of the invention comprises a second thickness in the form of at least one projection such as element 3 in FIG. 7F and at least one projection such as element 4 in FIG. 7F. Optionally, a patch of the invention comprises a first thickness such as element 1 in FIG. 7F. Optionally, a first thickness is the base thickness of the patch (element 1 of FIGS. 7C and 7F). Optionally, a second thickness provides physical support to the patch. Optionally, a second thickness provides attachments means to the tympanic membrane such as element 3 in FIG. 7C.

Optionally, 0.1% to 20% of the surface area of the upper portion, the surface area bottom portion, or both comprises a projection. Optionally, 0.05% to 10% of the surface area of the upper portion, the surface area bottom portion, or both comprises a projection. Optionally, 0.5% to 20% of the surface area of the upper portion, the surface area bottom portion, or both comprises a projection. Optionally, 0.1% to 5% of the surface area of the upper portion, the surface area bottom portion, or both comprises a projection. Optionally, 1% to 10% of the surface area of the upper portion, the surface area bottom portion, or both comprises a projection. Optionally, 0.05% to 4% of the surface area of the upper portion, the surface area bottom portion, or both comprises a projection.

Optionally, the bottom surface is free of projections as described herein. Optionally, the bottom surface comprises pores. Optionally, the bottom portion has a uniform surface.

Optionally, the surface area of the upper portion, the surface area of the bottom portion, or both comprises a cell adhesion molecule. Optionally, the surface area of the upper portion, the surface area of the bottom portion, or both comprises: an anti-inflammatory agent, an antibacterial agent, an antiseptic agent, a healing enhancing agent, factor XIII, Thrombin, an adherence enhancer agent or any combination thereof. Optionally, the surface area of the upper portion, the surface area of the bottom portion, or both comprises a chondrocyte, a fibroblast, a chondrocyte precursor, a fibroblast precursor, a mesenchymal cell, or any combination thereof.

Optionally, the patch is dried. Optionally, the patch is hydrated. Optionally, the patch is dried.

Optionally, provided herein a kit comprising the biodegradable patch, suspended in a sterile wetting solution, and instructions for use in repairing a perforation in a tympanic membrane in a mammal. Optionally, provided herein the sterile wetting solution can consist of saline, calcium chloride, an anti-inflammatory agent, an antibacterial agent, an antiseptic agent, a healing enhancing agent, factor XIII, Thrombin, an adherence enhancer agent or any combination thereof.

Optionally, provided herein method of repairing a perforation in a tympanic membrane in a mammal, the method comprising: providing biodegradable patch and implanting the biodegradable patch in a mammal's tympanic membrane.

In another specific embodiment, the patch is of a single layer with predefined thickness. In another specific embodiment, the patch is of a single layer with at least two predefined thicknesses. In another specific embodiment, the patch is a laminate of two or more layers.

In another specific embodiment, the patch is hydrated prior to contacting with the tympanic membrane. Optionally, the patch is between about 20 micrometers and about 200 micrometers in thickness in the dry state. Optionally, the patch is between about 10 micrometers and about 140 micrometers in thickness in the dry state. Optionally, the patch is between about 10 micrometers and about 100 micrometers in thickness in the dry state. Optionally, the patch is between about 80 micrometers and about 400 micrometers in thickness in the dry state.

Optionally, a patch is at least 20 microns in thickness. Optionally, the first thickness is 20 to 80 microns thick. Optionally, the first thickness is 30 to 60 microns thick. Optionally, the measures of thickness and density are provided for the dry state or the substantially dried state of the patch. Optionally, the measures of thickness and density are provided for the hydrated state of the patch.

Optionally, a hydrated patch has a thickness between about 0.05 and 0.8 mm. Optionally, a hydrated patch has a thickness between about 0.1 and 0.8 mm. Optionally, a hydrated patch has a thickness between about 0.1 and 0.5 mm. Optionally, a first thickness of the hydrated patch has a thickness between about 0.05 to 0.4 mm. Optionally, a first thickness of the hydrated patch has a thickness between about 0.1 to 0.3 mm.

Optionally, a dry or a substantially dry patch (such as but not limited to a collagen of all types, either non cross-linked or cross-linked) has a density of 0.05 $g/cm^2$ to about 1 $g/cm^2$. Optionally, a dry or a substantially dry patch has a density of 0.05 $g/cm^2$ to about 0.8 $g/cm^2$. Optionally, a dry or a substantially dry patch has a density of 0.1 $g/cm^2$ to about 0.8 $g/cm^2$. Optionally, a dry or a substantially dry patch has a density of 0.1 $g/cm^2$ to about 0.5 $g/cm^2$.

Optionally, a patch is a scaffold. Optionally, a patch as described herein is adapted to be inserted via the middle ear and onto the inner side of the tympanic membrane. Optionally, a patch as described herein is adapted to withstand pressure changes in the ear cavity, as well as shear forces. Optionally, a patch as described herein is adapted to adhere to the edges of the tympanic membrane tissue, in order to allow for hermetic closure. Optionally, a patch as described herein is adapted to promote cell proliferation, cell migration and cell differentiation. Optionally, a patch as described herein is adapted to promote cell migration.

Optionally, the upper portion, the lower portion or both sides of the patch comprise rough and/or ragged surface which promotes adherence to the tympanic membrane and/or adherence of cells attached to the patch. Optionally, the upper portion, the lower portion or both sides of the patch comprise sub-micron and/or micron sized pores which promote adherence to the tympanic membrane and/or adherence of cells attached to the patch.

Optionally, the upper portion, the lower portion or both sides of the patch comprise 0.1 micrometer to 1 micrometer (diameter of the pore) pores which promote adherence to the tympanic membrane and/or adherence of cells attached to the patch. Optionally, the upper portion, the lower portion or both sides of the patch further comprise a graft layer laminated to a surface of the patch. Optionally, a graft layer is a layer which promotes cell survival, cell proliferation, cell maturation, cell migration or any combination thereof. Optionally, a graft layer is composed of a hydrogel. Optionally, a graft layer further comprises cell adhesion molecules, growth factors, proteins, carbohydrates, cytokines, chemokines or any combination thereof.

Optionally a patch as described herein is in a folded position (for insertion) or in an open position (placement position). Optionally a patch as described herein is pre packed (folded) and contained within an ear/tympanic membrane insertion device which spreads flat the patch in proximity to the tympanic membrane. Optionally, a patch as described herein has structural memory of its flat appearance as well as strength and flexibility withstanding the folding through shelf life storage. Optionally, a patch as described herein comprises a string or an anchor for attaching it to the insertion device (see FIG. 7A).

Optionally a patch as described herein comprises a concentric cord, string, filament, or wire for attaching it to the insertion device. Optionally, a patch as described herein comprises an absorbable spring (FIG. 7B) serving as a tissue anchor which is screwed into the tympanic membrane thus connecting the patch to the tympanic membrane. Optionally, an absorbable sponge is attached to a surface of the bottom portion (facing the tympanic membrane) of the patch to fixate the patch onto the tympanic membrane (see FIG. 7C).

Optionally, a patch as described herein is rounded. Optionally, a patch as described herein has a shape of a circle. Optionally, a patch as described herein has a shape of a rectangular. Optionally, a patch as described herein has a shape of an ellipse.

Optionally, a patch as described herein comprises suture on its upper portion, on its lower portion or both (see FIG. 7D). Optionally, a patch comprising a suture is made by electrospinning of the hydrogel polymer. Optionally, a suture is connected to a first thickness. Optionally, a suture is further connected to a first thickness via the threads (element 2 in FIG. 7F). Optionally, the threads (element 2 in FIG. 7F) ensure that the inserted folded patch is fully open upon approach to the tympanic membrane. Optionally, the threads (element 2 in FIG. 7F) ensure that the inserted folded patch is fully opened upon attachment to the tympanic membrane. Optionally, the threads are stretchers, stretching-opening the patch upon or prior to contacting the patch with the tympanic membrane.

Optionally, the height of the suture is at least 5 times the thickness of the thickest portion of the upper portion of the patch, lower portion of the patch, or both. Optionally, the height of the suture is at least 50 times the thickness of the thickest portion of the upper portion of the patch, lower portion of the patch, or both. Optionally, the height of the suture is 10 to 50 times the thickness of the thickest portion of the upper portion of the patch, lower portion of the patch, or both. Optionally, the height of the suture is 20 to 2000 times the thickness of the thickest portion of the upper portion of the patch, lower portion of the patch, or both. Optionally, the height of the suture is 20 to 500 times the thickness of the thickest portion of the upper portion of the patch, lower portion of the patch, or both. Optionally, the height of the suture is 100 to 800 times the thickness of the thickest portion of the upper portion of the patch, lower portion of the patch, or both.

Optionally, the height of the suture is 500 to 4000 times the thickness of the thickest portion of the upper portion of the patch, lower portion of the patch, or both. Optionally, the height of the suture is 500 to 1500 times the thickness of the thickest portion of the upper portion of the patch, lower portion of the patch, or both. Optionally, the height of the suture is 200 to 1200 times the thickness of the thickest portion of the upper portion of the patch, lower portion of the patch, or both. Optionally, the height of the suture is 400 to 1000 times the thickness of the thickest portion of the upper portion of the patch, lower portion of the patch, or both.

Optionally, the polymer hydrogel or "hydrogel" is an alginate or a salt thereof. Optionally, a suitable polymer hydrogel according to the invention comprises a polysaccharide. Optionally, a suitable polymer hydrogel according to the invention comprises a polyphosphazene. Optionally, a suitable polymer hydrogel according to the invention comprises a polyacrylate. Optionally, a suitable polymer hydrogel according to the invention comprises a poly(oxyethylene)-poly(oxypropylene) Optionally, a suitable polymer hydrogel according to the invention comprises a poly(oxyethylene)-poly(oxypropylene). Optionally, a suitable polymer hydrogel according to the invention comprises any combination of: chitosan, polyesters, poly urethans, polyimides, poly carbonate, PLLA, PLA, PLGA.

Optionally, a suitable polymer hydrogel according to the invention comprises a poly(phosphazene). Optionally, a suitable polymer hydrogel according to the invention comprises a poly(acrylic acid). Optionally, a suitable polymer hydrogel according to the invention comprises a poly(methacrylic acid). Optionally, a suitable polymer hydrogel according to the invention comprises a poly(vinyl amine). Optionally, a suitable polymer hydrogel according to the invention comprises a poly(vinyl pyridine). Optionally, a suitable polymer hydrogel according to the invention comprises a poly(vinyl imidazole).

Optionally, a suitable polymer hydrogel according to the invention comprises a polyphosphazene. Optionally, a suitable polymer hydrogel according to the invention comprises a collagen. Optionally, a suitable polymer hydrogel according to the invention comprises ethylene diamine, poly (acrylic acids), poly(methacrylic acids), copolymers of acrylic acid and methacrylic acid, poly(vinyl acetate), sulfonated polymers, or any combination thereof. Optionally, the hydrogel is alginate, chitosan, pluronic, collagen, agarose, or any combination thereof.

Optionally, a suitable polymer hydrogel according to the invention comprises collagen. Optionally, a suitable polymer hydrogel according to the invention comprises non-protease-treated collagen. Optionally, the collagen is not cross-linked, e.g., the collagen is not fixed. Optionally, the collagen is partially cross-linked. Optionally, the collagen is cross-linked. Optionally, the collagen is substantially dry prior to use within a patient. Optionally, the collagen comprises 25% or less water by weight. Optionally, the collagen comprises 20% or less water by weight. Optionally, the collagen comprises 15% or less water by weight. Optionally, the collagen comprises 2% to 20% water by weight.

Optionally, collagen is placenta-derived amniotic derived or chorion derived. Optionally, collagen is derived from a transgenic plant. Optionally, one of skill in the art can readily choose a collagen from various sources.

Optionally, collagen is a mixture of collagen types I, III and IV. Optionally, a hydrogel or a collagen further comprises fibrin, fibronectin, elastin, glycosaminoglycans, proteoglycans, or any combinations thereof.

Optionally, a patch as described herein comprises a cell growth factors such as but not limited to PDGF, VEGF, FGF, TGFβ, an interleukin, a cytokine or any combination thereof. Optionally, a patch as described herein induces the migration of fibroblasts and macrophages, and thus the promotion of wound healing.

Optionally, a patch as described herein is impregnated or coated with a bioactive compound, such as but not limited to: small organic molecules (e.g., drugs), antibiotics (such as Clindamycin, Minocycline, Doxycycline, Gentamycin), hormones, growth factors, anti-tumor agents, anti-fungal agents, anti-viral agents, pain medications, anti-histamines, anti-inflammatory agents, anti-infectives including but not limited to metals, metal-oxides and/or silver (such as silver salts, including but not limited to silver nitrate and silver sulfadiazine), elemental silver, antibiotics, bactericidal enzymes (such as lysozyme), wound healing agents (such as cytokines including but not limited to PDGF, TGF; thymosin), hyaluronic acid as a wound healing agent, wound sealants (such as fibrin with or without thrombin), cellular attractant and scaffolding reagents (such as added fibronectin) and the like.

Optionally, a patch as described herein is impregnated or coated with small organic molecules such as specific inhibitors of particular biochemical processes e.g., membrane receptor inhibitors, kinase inhibitors, growth inhibitors, anticancer drugs, antibiotics, etc.

Optionally, a patch as described herein is impregnated or coated with a macrolide (e.g., tobramycin (Tobi®)), a cephalosporin (e.g., cephalexin (Keflex®)), cephradine (Velosef®)), cefuroxime (Ceftin®, cefprozil (Cefzil®), cefaclor (Ceclor®), cefixime (Suprax® or cefadroxil (Duricef®), a clarithromycin (e.g., clarithromycin (Biaxin)), an erythromycin (e.g., erythromycin (EMycin®)), a penicillin (e.g., penicillin V (V-CillinK® or Pen VeeK®)) or a quinolone (e.g., ofloxacin (Floxin®), ciprofloxacin (Cipro®) ornorfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, arndinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Optionally, a patch as described herein is impregnated or coated with an antifungal agent. Suitable antifungal agents include but are not limited to amphotericin B3 itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

Optionally, a patch as described herein is impregnated or coated with an anti-inflammatory agent. Useful antiinflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofm; and other anti-inflammatory agents including, but not limited to, methotrexate, colchicine, allopurinol, probenecid, sulfinpyrazone and benzbromarone.

Optionally, a patch as described herein is impregnated or coated with an antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons.

Optionally, a patch as described herein is impregnated or coated with a cytokine receptor modulator. Examples of cytokine receptor modulators include, but are not limited to, soluble cytokine receptors (e.g., the extracellular domain of a TNF-α receptor or a fragment thereof, the extracellular domain of an IL-10 receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8JL-9, IL-10, IL-I1, IL-12, IL-15, TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-10 antibodies, anti-IL-6 antibodies, anti-IL-8 antibodies (e.g., ABX-IL-8 (Abgenix)), and anti-IL-12 antibodies). In a specific embodiment, a cytokine receptor modulator is IL-4, IL-IO, or a fragment thereof. Optionally, a cytokine receptor modulator is an anti-IL-1 antibody, anti-IL-6 antibody, anti-IL-12 receptor antibody, or anti-TNF-α antibody. Optionally, a cytokine receptor modulator is the extracellular domain of a TNF-α receptor or a fragment thereof. In certain embodiments, a cytokine receptor modulator is not a TNF-α antagonist.

Optionally, a patch as described herein is impregnated or coated with proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides.

Optionally, a patch as described herein is impregnated or coated with a cytokine. Examples of cytokines include, but are not limited to, colony stimulating factor 1 (CSF-I), interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), insulin-like growth factor 1 (IGF-I), platelet derived growth factor (PDGF), erythropoietin (Epo), epidermal growth factor (EGF), fibroblast growth factor (FGF) (basic or acidic), granulocyte macrophage stimulating factor (GM-CSF), granulocyte colony stimulating factor (G-CSF), heparin binding epidermal growth factor (HEGF), macrophage colony stimulating factor (M-CSF), prolactin, and interferon (IFN), e.g., IFN-alpha, and IFN-gamma), transforming growth factor alpha (TGF-α), TGFβ1, TGFβ2, tumor necrosis factor alpha (TNF-α), vascular endothelial growth factor (VEGF), hepatocyte growth factor (HGF), etc.

Optionally, a patch as described herein is impregnated or coated with a hormone. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins. Examples of β-interferons include, but are not limited to, interferon β 1-a and interferon β 1-b.

Optionally, a patch as described herein is impregnated or coated with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

Optionally, a patch as described herein is impregnated or coated with an immunomodulatory agent, including but not limited to methothrexate, leflunomide, cyclophosphamide, cyclosporine A, macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methothrexate, leflunomide, cyclophosphamide, Cytoxan, Imrnuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. Examples of T cell receptor modulators include, but are not limited to, anti-T cell receptor antibodies (e.g., anti-CD4 antibodies (e.g., cM-T412 (Boeringer), IDEC-CE9.ÏS (DEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131(IDEC)), anti-CD52 antibodies (e.g., CAMPATH IH (Ilex)), anti-CD2 antibodies, anti-CD1 Ia antibodies (e.g., Xanelim (Genentech)), and anti-B7 antibodies (e.g., IDEC-114) (IDEC))) and CTLA4-immunoglobulm. Optionally, a patch as described herein is impregnated or coated with an immunomodulatory compound known as IMiD.

Optionally, impregnation is accomplished by immersing the patch in a solution of the bioactive compound of the desired concentration for a time sufficient to allow the patch to absorb and to equilibrate with the solution.

Making the Patch

Optionally, the patch of the invention for repairing a perforation in a tympanic membrane is made by providing a mold having a defined, e.g., predetermined, negative shape of the patch. Optionally, the methods include introducing a liquid hydrogel composition into the mold; inducing gel formation to solidify the liquid hydrogel composition to form a hydrogel patch; and removing the hydrogel patch from the mold after gel formation, wherein the construct has a shape suitable for repairing a perforation in a tympanic membrane.

Optionally, the hydrogel polymer patch is produced by electrospinning of a polymer.

Optionally, the methods further include suspending cells, cell adhesion molecule, a cell growth factor, an antibiotic, an antibacterial agent, an anti-inflammatory agent, an antiseptic agent or any combination thereof in the liquid hydrogel to form a composition or a patch as described herein. Optionally, gel formation is induced by contacting the liquid hydrogel with a suitable concentration of a divalent cation.

Repairing a Tympanic Membrane

The present invention provides a method for the repair of a tympanic membrane using a patch as described herein. In one embodiment, the tympanic membrane to be repaired has a deformity. Optionally, the deformity is an acute perforation. Optionally, the deformity is a chronic perforation. Optionally, the deformity relates to cholesteatoma. Optionally, the deformity is caused by a tumor in the middle ear. Optionally, the deformity is a disease of the tympanic membrane such as dimeric drum, a retraction, a retraction pocket (i.e., pocket formed in the eardrum resulting from retraction of the tympanic membrane into the middle ear cavity due to loss of pressure in the middle ear cavity), or tympanosclerosis, and the like.

Optionally, repair of a tympanic membrane deformity or perforation encompass contacting the tympanic membrane with a patch for a time sufficient to heal the tympanic membrane deformity, for a time sufficient to measurably improve one or more aspects of the tympanic membrane deformity or perforation, or for a time sufficient to lessen the worsening of one or more aspects of the tympanic membrane deformity, as compared to a tympanic membrane not contacted with a patch. Optionally, the terms "deformity" and "perforation" are used interchangeably.

Optionally, aspects of a tympanic membrane deformity include objectively measurable criteria, such as ability of the tympanic membrane to transmit sound, hearing loss in decibels, appearance of the tympanic membrane or surrounding tissue, ingrowth of epithelial tissue into or around a perforation in the tympanic membrane, etc., or subjective criteria, such as a sense of improved hearing, lessening of discomfort or pain, etc.

Optionally, the deformity is a perforation. Optionally, repairing a tympanic membrane includes totally or partially covering the perforation with a patch.

Optionally, a patch as described herein is placed or implanted in-situ with an insertion instrument for implanting a tympanic membrane patch. Optionally, insertion instruments for implanting a tympanic membrane patch are known to one of skill in the art.

Figure 8A:
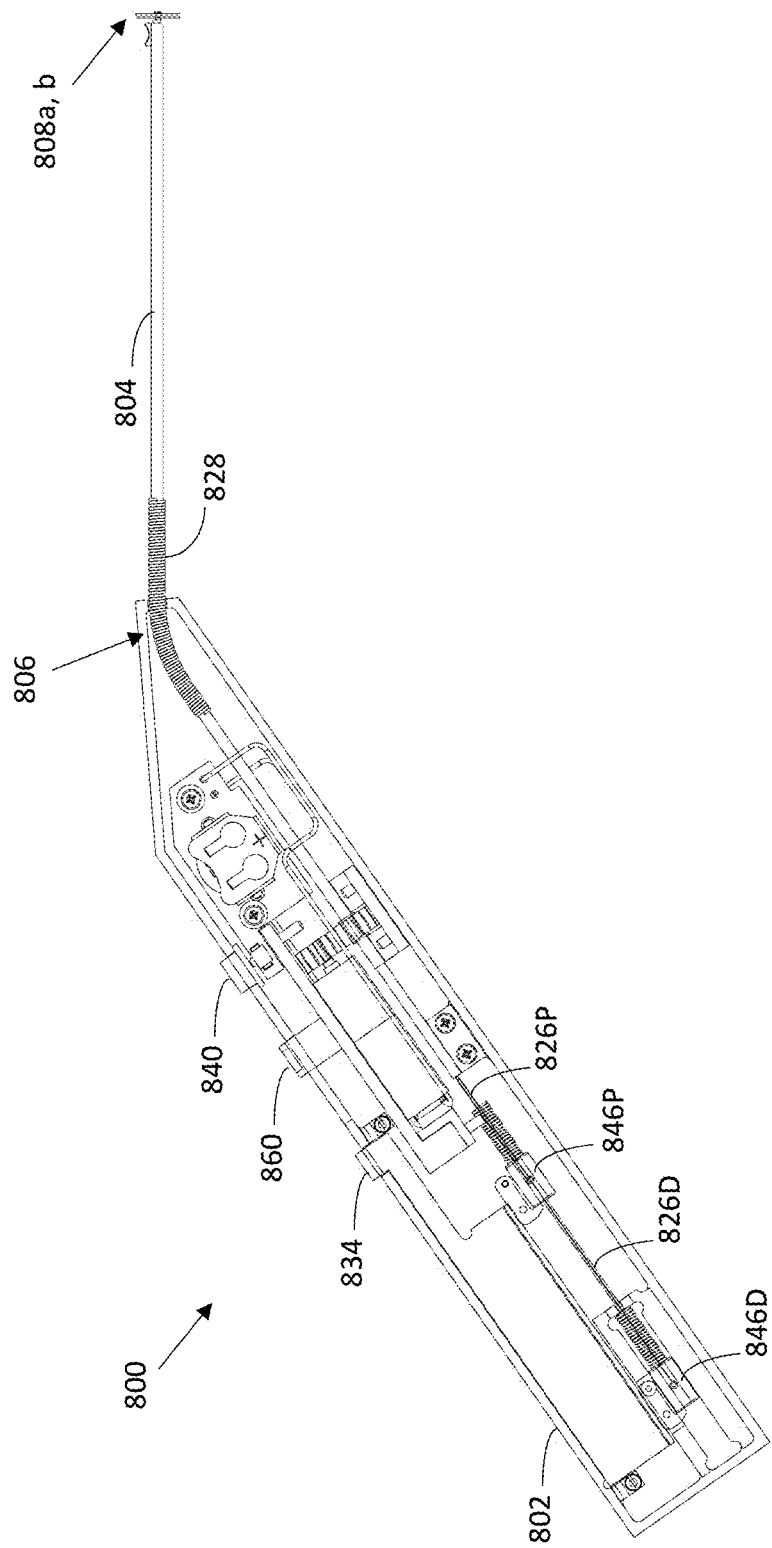
FIGS. 8A-8F show multiple views of a tympanoplatic patch applicator, in accordance with another embodiment.
Figure 8B:
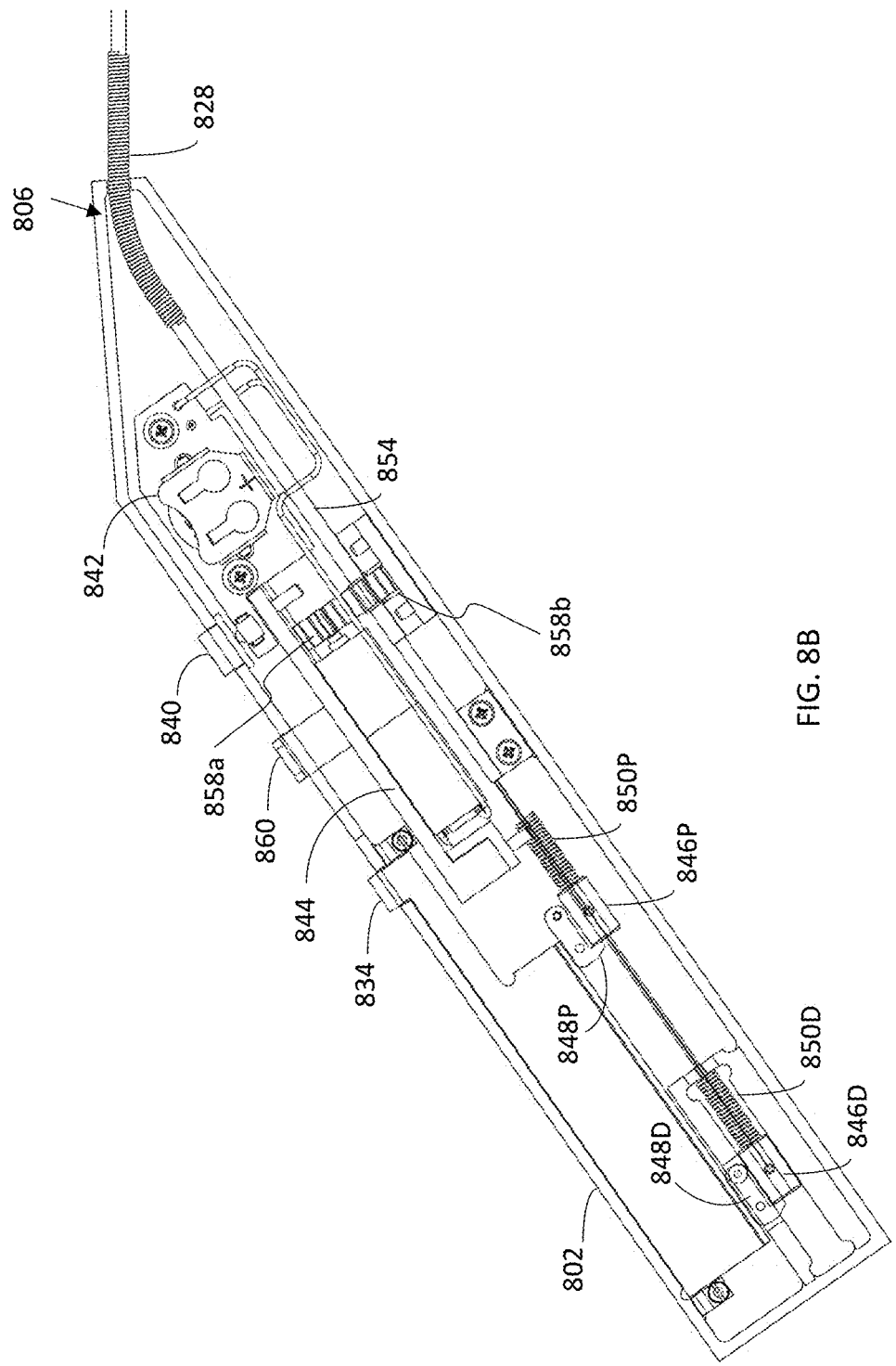
Figure 8C:
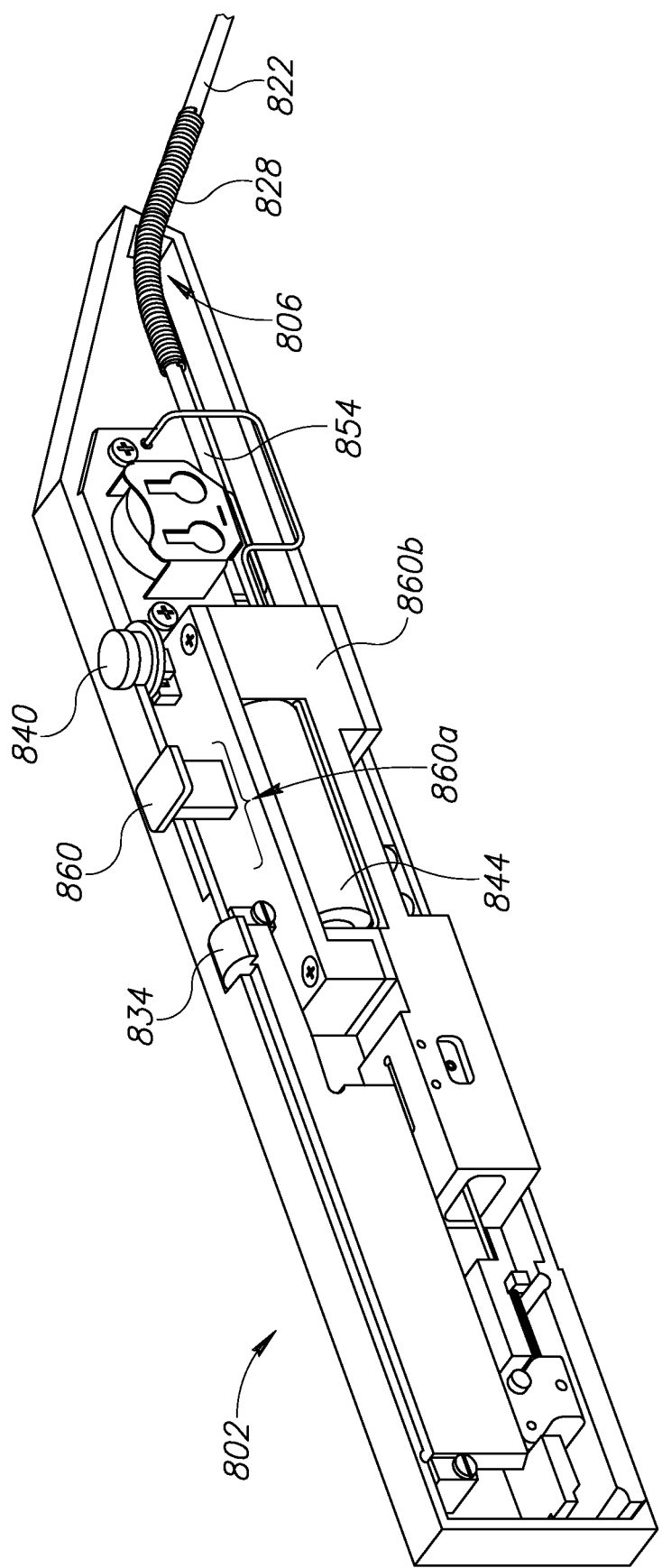
Figure 8D:
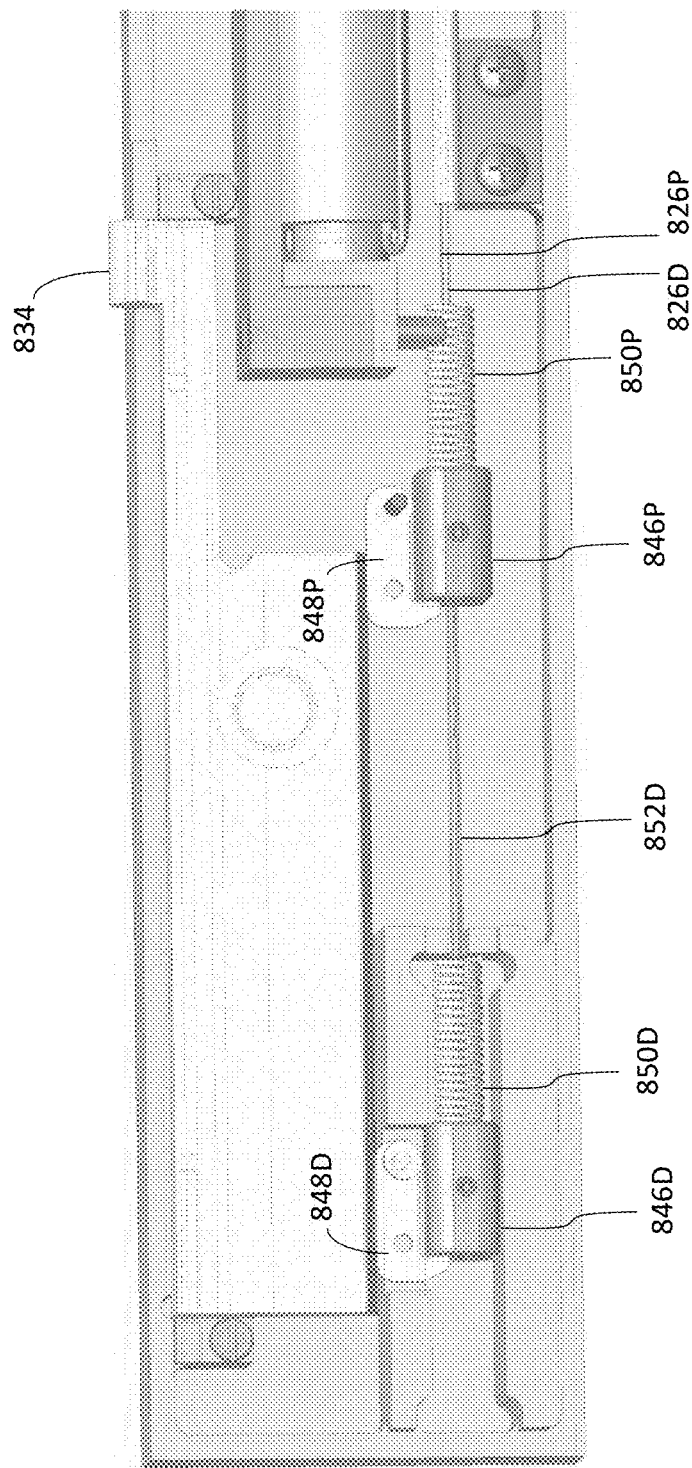

Reference is now made to FIGS. 8A-8F which illustrate various views of an applicator 800 for repairing a perforated tympanic membrane, in accordance with an embodiment. FIG. 8A illustrates a cross-section of the entire applicator 800 having a proximally disposed handle 802 and distally disposed deployment stem 804. FIG. 8B-8D illustrates detailed cross-sectional views of handle 802, and FIGS.

8E-8F illustrate a detailed cross-sectional and perspective view, respectively, of the distal tip of stem 804. Applicator 800 is substantially similar to applicator 100 described above, and it is to be understood the description that follows relates to the differences between applicator 800 and applicator 100, and that unless otherwise specified, their structure and function are substantially the same.

Referring to FIG. 8A, handle 802 is provided with a deployment control mechanism comprising actuators 834 and 840, and 860. Deployment stem 804 may include multiple nested, telescoping sleeves connected to handle 802.

Figure 8E:
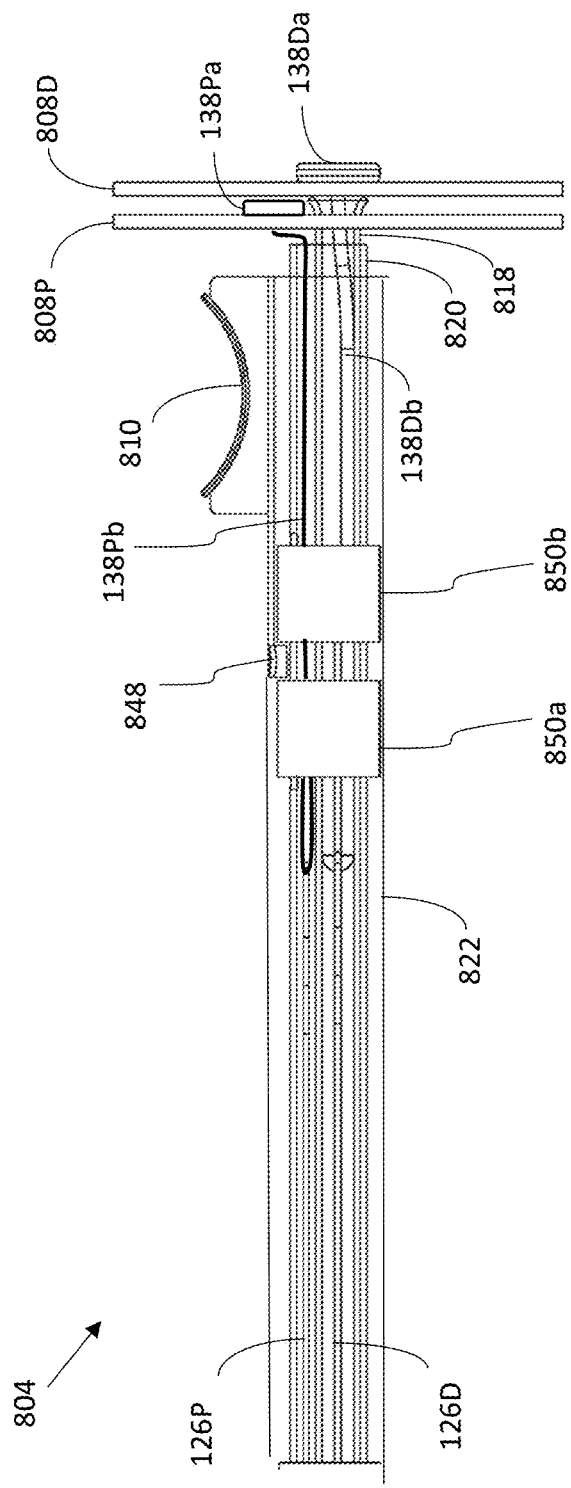
Figure 8F:
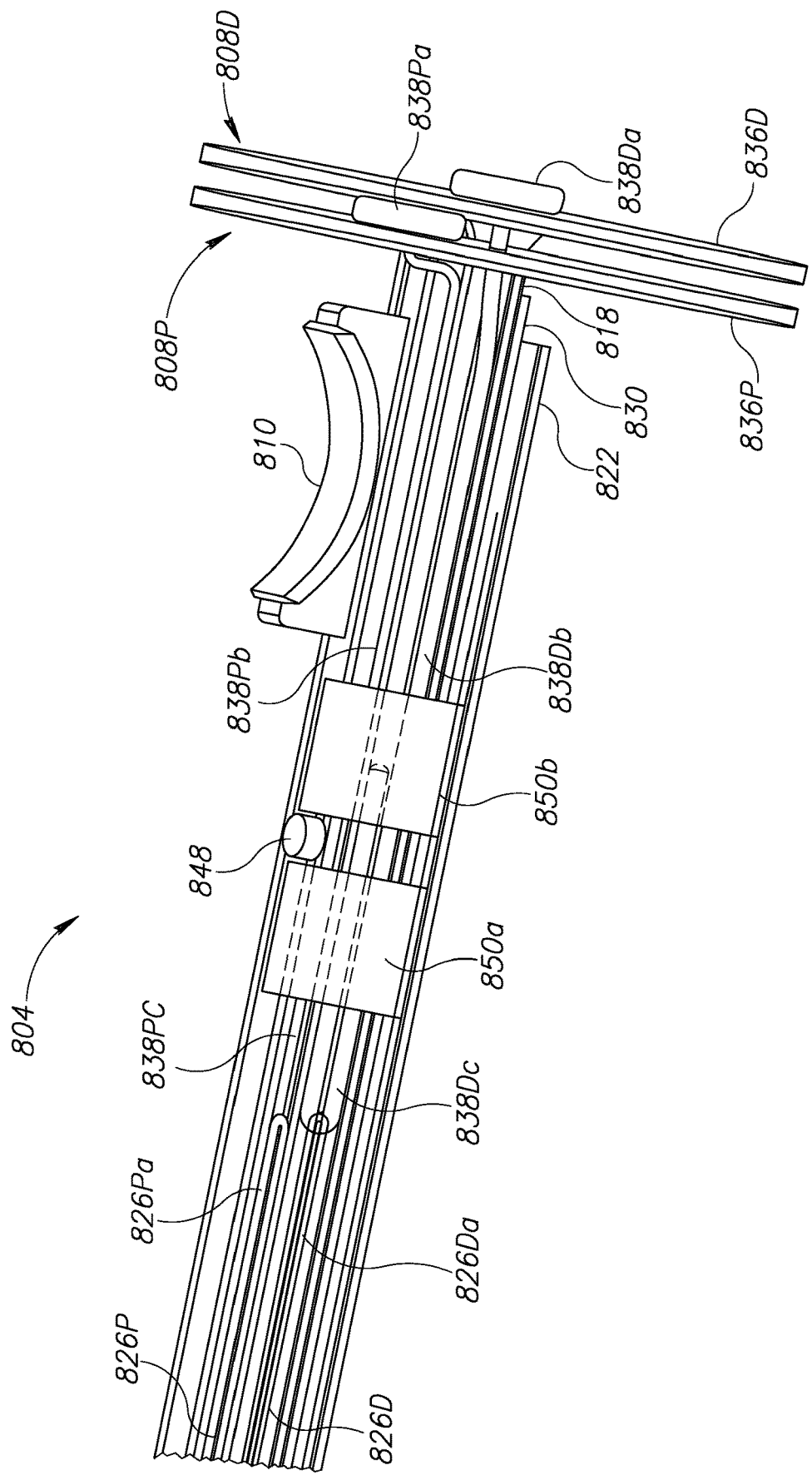

Referring to FIGS. 8E-8F, the multiple nested and telescoping sleeves may include an inner sleeve 818, a middle sleeve 820 encasing inner sleeve 818, and an outer sleeve 822 encasing middle sleeve 820, similar to sleeves 118, 120, and 122 described above. Two patches, a distally disposed patch 808D superimposed with a proximally disposed patch 808P may be affixed to the distal end of the deployment stem 804. Distal patch 808D may be affixed via a distal actuation filament 826D embedded within the inner sleeve 818 of deployment stem 804, thereby affixing distal patch 808D to the distal end of the inner sleeve 818, and proximal patch 808P may be affixed via a proximal actuation filament 826P embedded within middle sleeve 820, thereby affixing proximal patch 808P to the distal end of the middle sleeve 820. Filaments 826P and 826D may be made of any fiber suitable for withstanding a tensile force, such as but not limited to metallic wire, or thread, such as may be made of nylon or other suitable material.

Distal patch 808D may be disposed with a distal patch cord 838Db that engages with distal filament 826D within inner sleeve 818, and proximal patch 808P may be disposed with a proximal patch cord 838Pb that engages with proximal filament 826P within middle sleeve 820, external to inner sleeve 818, thereby securing patches 808D and 808P to the distal ends of sleeves 818 and 820, respectively. Cords 838Db and 838Pb may correspond to cord 138 described above. As with patch 108, cords 838Db and 838Pb may have a wider distal ends 838Da and 838Pa attaching cords 838Db and 838Pb to disks 836D and 836P of patches 808D and 808P, respectively, and which may allow pulling any of patches 808D and 808P proximally by pulling on filaments 826D and 826P, and/or by retracting sleeves 818 and 820 proximally Patches 808D and 808P are constructed from a resilient material that flexes to fit through the perforation, and restores its original shape when emerging from the perforation.

Optionally, the filaments may engage with the cords as follows: a proximal end 838Dc of distal patch cord 838Db may loop through a looped distal end 826Da of the distal filament 826D in the inner sleeve 818, and the proximal end 838Pc of the proximal patch cord 838Pb may loop through a looped distal end 826Pa of the proximal filament 826P in the middle sleeve 820. Proximal ends 838Dc and 838Pc may be unattached, such that withdrawing filaments 826D and 826P may unravel the engagement. Filaments 826D and 826P may each be configured as a doubled over filament that is fused along its length proximally, leaving only a relatively small unfused portion at the distal end, to form loops 826Da and 826Pa.

Deployment actuators 834 and 860 may control the filament-based deployment system as follows:

Referring to FIGS. 8A-8D, actuator 860 may be positioned with an elongated niche 860a within handle 802, allowing actuator 860 to slide distally and proximally within niche 860a. Actuator 860 may be integrally connected to a case 860b, such that sliding actuator 860 along niche 860a moves case 860b distally and proximally, accordingly. Case 860b may enclose a debridement mechanism comprising a motor 844 and a gear wheel mechanism, comprising two engaged gear wheels 858a and 858b, mechanically connected to a blade pushing tube 854, which is in turn connected to spring 828 that is connected to outer sleeve 822, similar to spring 128 and sleeve 122 described above. Referring to FIG. 8E, outer sleeve 822 connects to middle sleeve 820 via a pin 862 sandwiched between two disks 864a-b. It may be appreciated that other connecting means may be used. Thus sliding actuator 860 distally and proximally within niche 860a advances and retracts blade pushing tube 854 which advances and retracts outer and middle sleeves 822 and 820 over bend 806 via spring 828, accordingly. Optionally, inner sleeve 818 is not connected to sleeves 822 and 820, and moves independently. Optionally, a strengthening tube (not shown) is nested between the middle and outer sleeves 820 and 822, extending from blade pushing tube 854 distally. Spring 828 may encase the strengthening tube.

The operation of actuator 834 is illustrated in FIG. 8D. The proximal ends of filaments 826D and 826P may be each be anchored in handle 802 at filament bosses 846D and 846P, respectively. Springs 850D and 850P, each positioned distally to bosses 846D and 846P and enclosing filaments 826D and 826P, respectively, are provided to exert tension on filaments 826D and 826P responsive to actuator 834. Filament 826P may terminate at distally disposed boss 846P, and filament 826D may extend proximally via a tube 852D and terminate at proximally disposed boss 846D. Actuator 834 may be mechanically connected to bosses 846P and 846D via triggers 848P and 848D, such that a controlled downwards compression by actuator 834 pushes triggers 848P and 848D downwards, pushing bosses 846P and 846D, and exerting a tension on filaments 826D and 826P via springs 850D and 850P, accordingly. This tension retracts filaments 826D and 826P proximally, and unravels the proximal ends 838Dc, 838Dc of cords 838Db, 838Pb from the looped distal ends of filaments 826D and 826P, shown in FIG. 8E, causing distal patch cord 838Db and the proximal patch cord 838Pb to disengage from distal filament 826D and proximal filament 826P. This releases the distal patch and the proximal patch from the deployment stem 804.

Optionally, actuator 834 may be configured with multiple settings (not shown) that allow activating triggers 848P and 848D either separately, or together to control the retraction of filaments 826D and 826P, accordingly.

It may be appreciated that any of the features of device 100, such as but not limited to any of the rotation mechanisms provided for rotating any of sleeves 118, 120 may be implemented with device 800 for rotating any of sleeves 818, 820 accordingly.

Referring back to FIG. 8A, applicator 800 may be further provided with a debridement mechanism activated by actuator 840 configured with handle 802. The debridement mechanism includes blade pushing tube 854 and spring 828 mechanically connected to outer sleeve 822, and at least one protruding blade 810 disposed at the distal end of outer sleeve 822. Optionally, blade 810 is a single, concave arc-shaped blade such as shown in FIG. 8F. Alternatively, the at least one protruding blade may be configured as the convex blade pair 110a-b described above. Actuator 840 controls a power supply, such as battery 842, provided to drive motor 844. A gear wheel mechanism, comprising two engaged gear wheels 858a and 858b, mechanically connects motor 844 to blade pushing tube 854, transferring a rotation by motor 844 to sleeve 822 via blade pushing tube 854. Thus, activation by actuator 840 causes motor 844 to rotate thereby rotating protruding blade 810 disposed on sleeve 822, and causing a debridement of the circumference of the perforation of tympanic membrane when blade 822 is positioned at the tympanic membrane. Optionally, actuator 840 operates as a push button to activate the debridement.

Advantageously, the curvature of protruding blade 810 controls the penetration depth of blade 810 into the perforation. Similarly, the debridement mechanism may include a penetration depth controlling mechanism that limits the penetration depth of blade 810 by limiting the advancement of the outer sleeve 822 relative to inner sleeve 818. For example, the length of niche 860*a* may serve as a penetration depth controlling mechanism. As with the debridement mechanism of applicator 100, the debridement mechanism of applicator 800 may include a niche, such as may be formed between blade 810 and the outer surface of outer sleeve 822 for collecting any debrided tissue.

Reference is now made to FIGS. 9A-9H, which illustrate a method for repairing a perforated tympanic membrane using the filament-based deployment system of applicator 800. The filament-based deployment system may deploy patch 808D distally, at the internal side of a perforated tympanic membrane in the middle ear, and deploy patch 808P proximally, at the external side of the perforated tympanic membrane in the outer ear, thereby sandwiching the tympanic membrane between distally disposed patch 808D and the proximally disposed patch 808P.

Figure 9A:
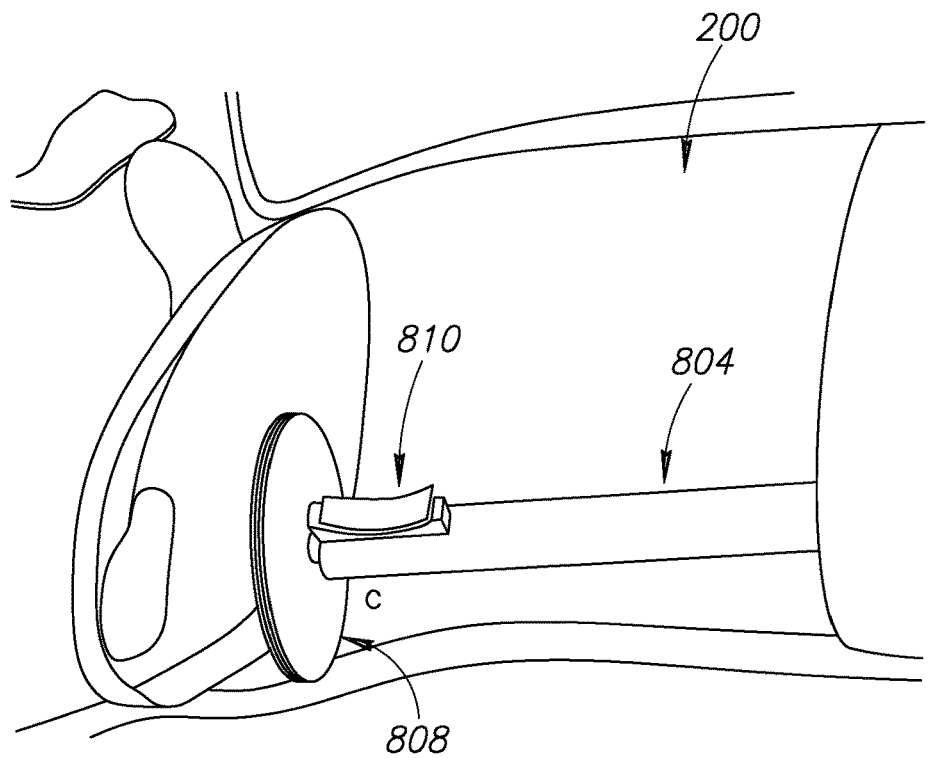
FIGS. 9A-9H illustrate a method for deploying two patches using the applicator of FIGS. 8A-8E.

Referring to FIG. 9A, deployment stem 804 may introduce the two patches 808D and 808D into the ear canal 200, such as via a speculum, 210, and penetrate the perforated tympanic membrane 202 with at least distally disposed patch 808D, via the inner sleeve.

Figure 9B:
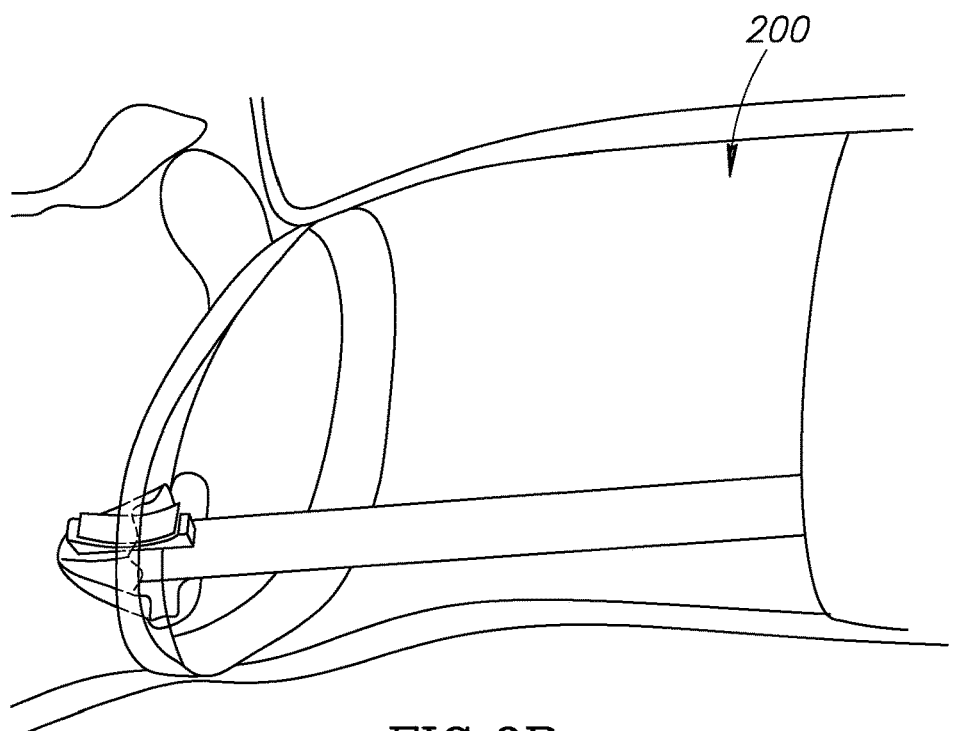

Referring the FIG. 9B, optionally, the perforated tympanic membrane 202 may be penetrated with both the distal patch together with the proximal patch, by inserting the middle sleeve encasing the inner sleeve through the perforation. The two patches may be constructed from a resilient material that flexes to fit through the perforation, and restores its original shape when emerging from the perforation. Optionally, the tympanic membrane may be penetrated with the distal end of stem 804 comprising the inner, middle, and outer sleeves 818, 820, and 822, with the distal ends of the three sleeves substantially aligned distally, bringing blade 810 into contact with the edge of the perforation.

Figure 9C:
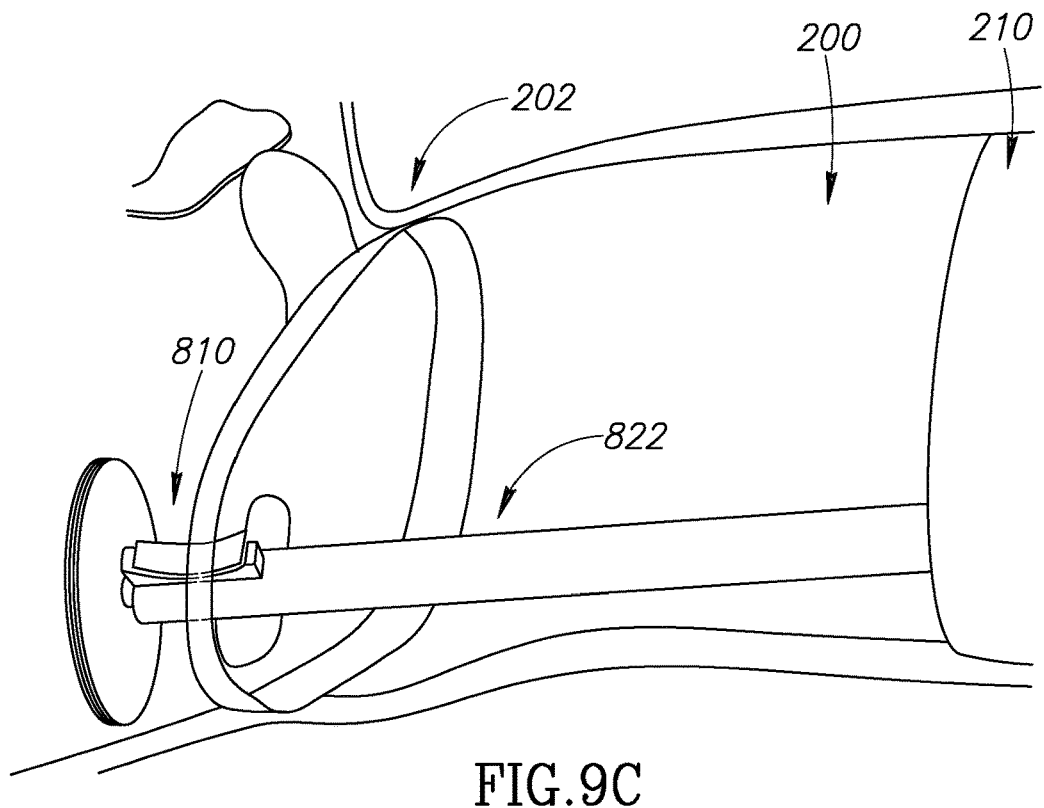

Referring to FIG. 9C, actuator 840 may be activated to perform a debridement of the circumference of the perforation. The debridement may be performed prior to the final deployment of the patches, to allow blood released from the debridement to subsequently serve as a glue for securing the patches to the tympanic membrane. Optionally the blade is concave, and the deployment stem is maneuvered to bring a concave edge of the blade with the edge of the perforation. With the blade 810 positioned thus, the outer sleeve may be rotated, thereby rotating the debridement blade about the circumference of the perforation. Optionally, debrided tissue resulting from the debridement may be collected in a niche formed between blade 810 and sleeve 810.

Figure 9D:
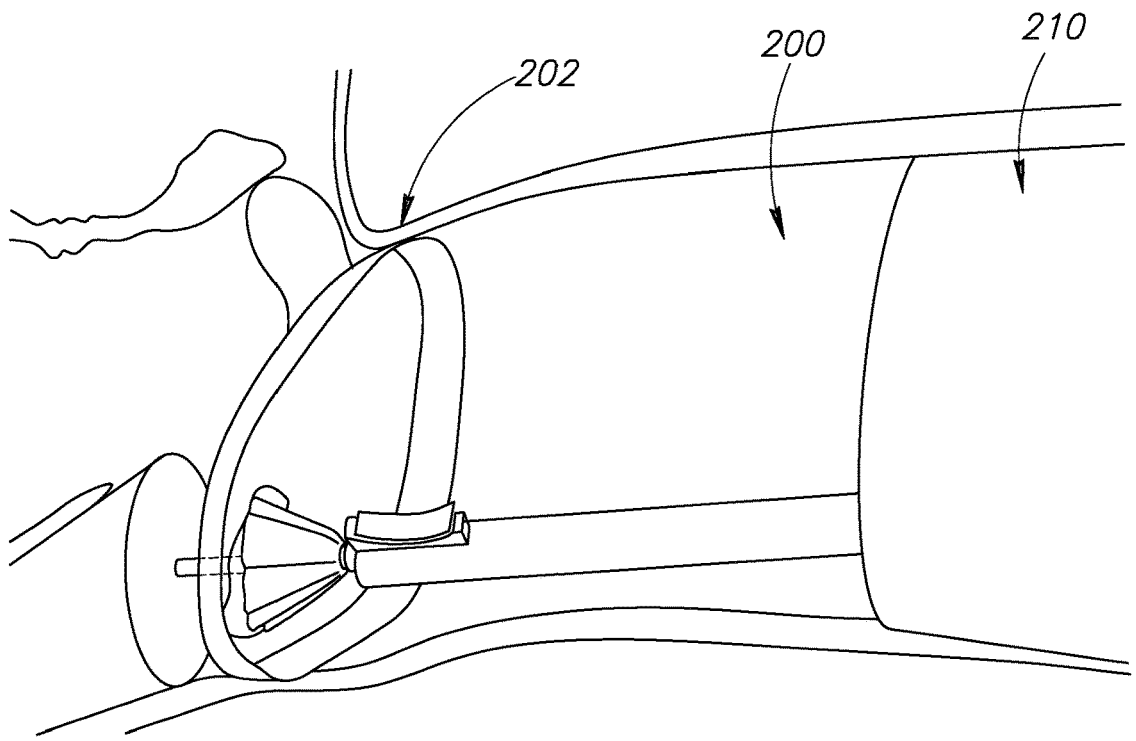

Referring to FIG. 9D, once the debridement is complete, actuator 860 may be retracted proximally within niche 860*a*, retracting outer sleeve 822 and middle sleeve 820 relative to the inner sleeve 818, to evacuated blade 810 and sleeves 822 and 820 from the middle ear through the debrided perforation. This serves to retract the proximal patch 808P from the middle ear through the perforation of the debrided tympanic membrane, and position the proximal patch 808P at the external side of the perforated tympanic membrane in the outer ear.

Figure 9E:
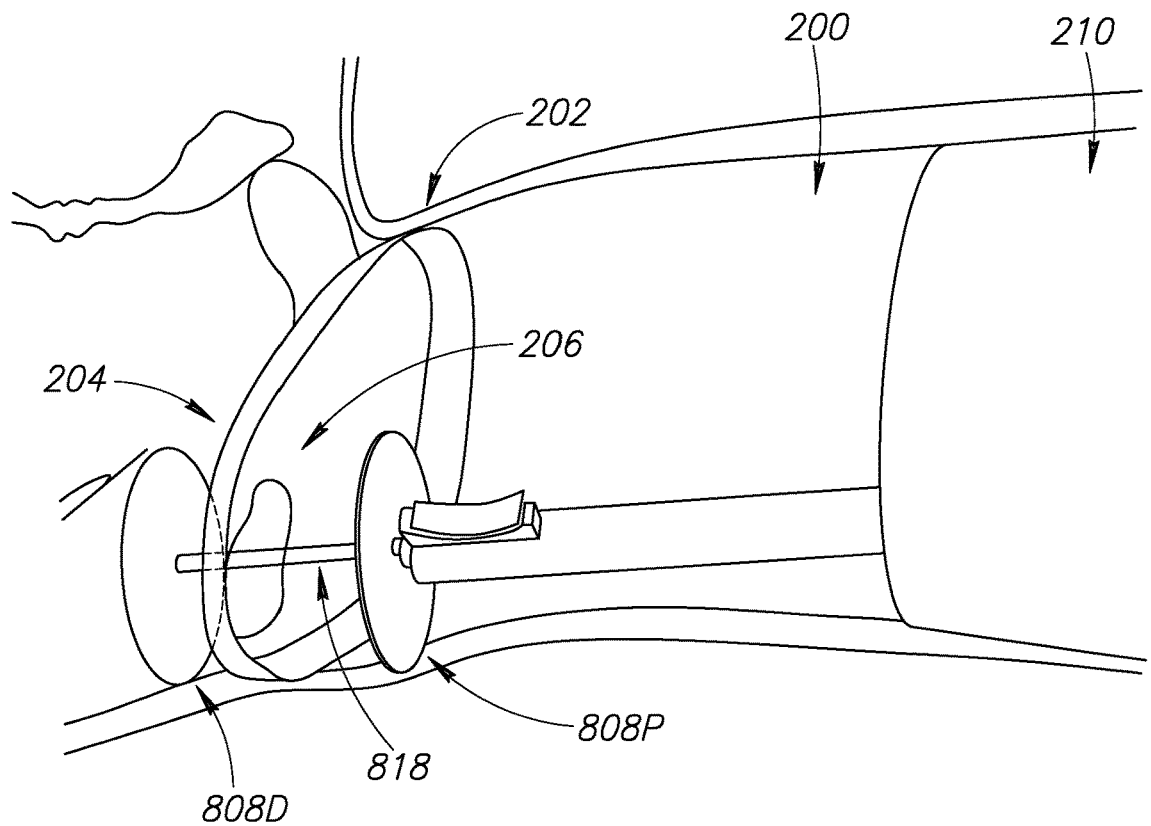

The proximal patch may flex to fit through the perforation (FIG. 9D), and restore its shape on emerging in the outer ear (FIG. 9E). The proximal patch 808P may possess a low surface tension towards the distal patch 808D, and thus patches 808P and 808D don't have a tendency to attach or adhere to each other.

Figure 9F:
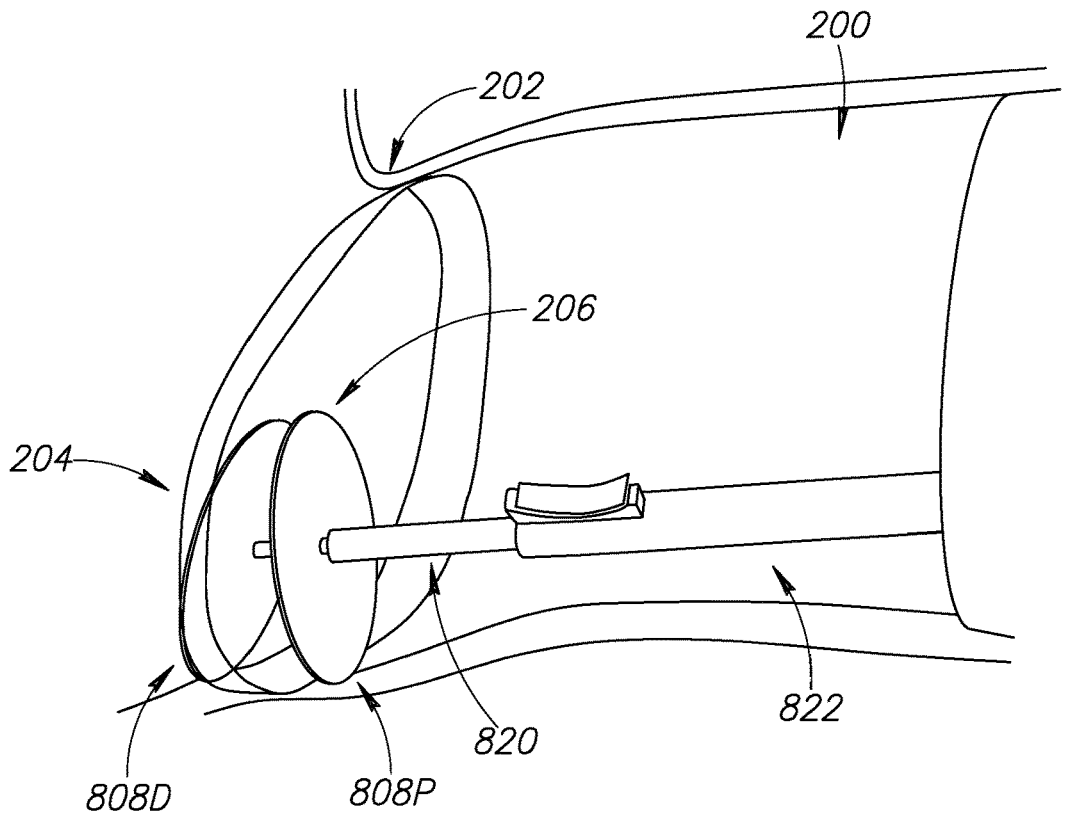

Referring to FIGS. 9E-9F, the distal patch 808D is now positioned at the internal side 204 of the perforated tympanic membrane 202 in the middle ear, and the proximal patch 808P is positioned at the external side 206 of the perforated tympanic membrane in the outer ear. At this stage, the distal patch 808D is still affixed to the inner sleeve 818, and positioned in the inner ear, with the tympanic membrane 202 positioned between the two patches (FIG. 9E).

Referring to FIG. 9F, the entire applicator may be retracted, retracting the deployment stem and pulling the inner sleeve with the distal patch 808D until the distal patch is flush with the internal side 204 of the perforated tympanic membrane 202.

Figure 9G:
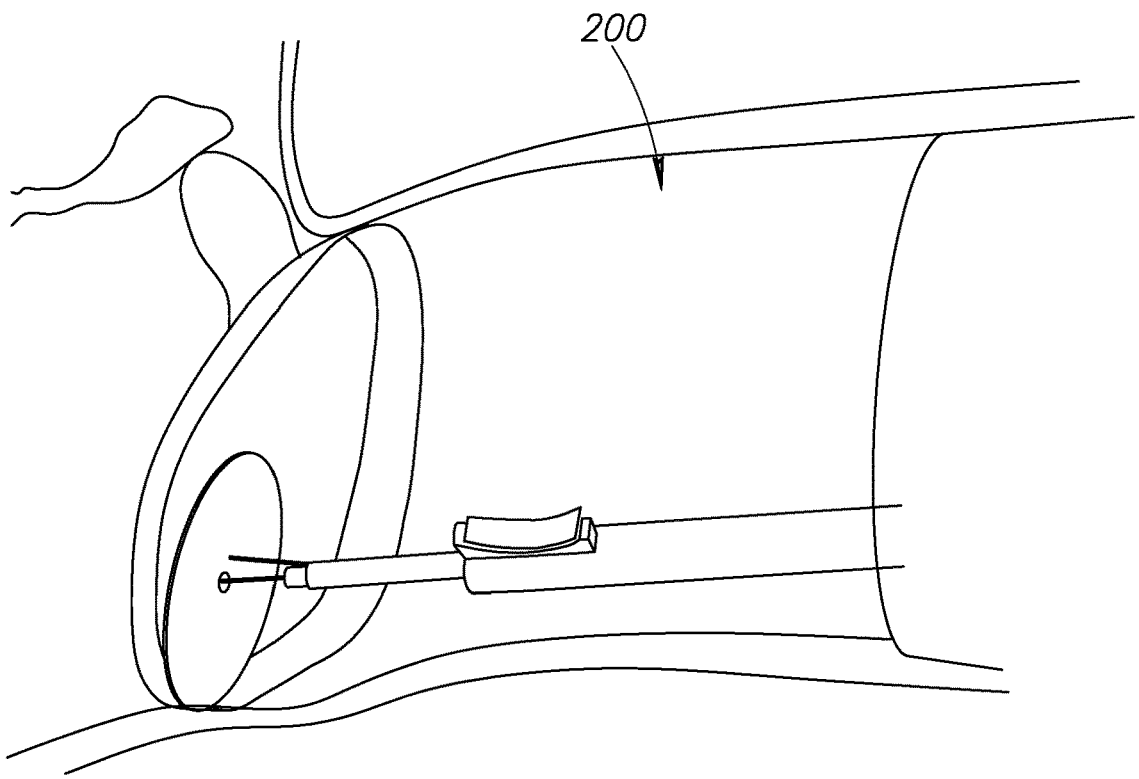

Referring to FIG. 9G, actuator 860 may be advanced distally within niche 860*a*, advancing sleeves 820 and 822 relative to the inner sleeve 818 until the proximal patch 808P is flush against the external side of the perforated tympanic membrane 206.

Figure 9H:
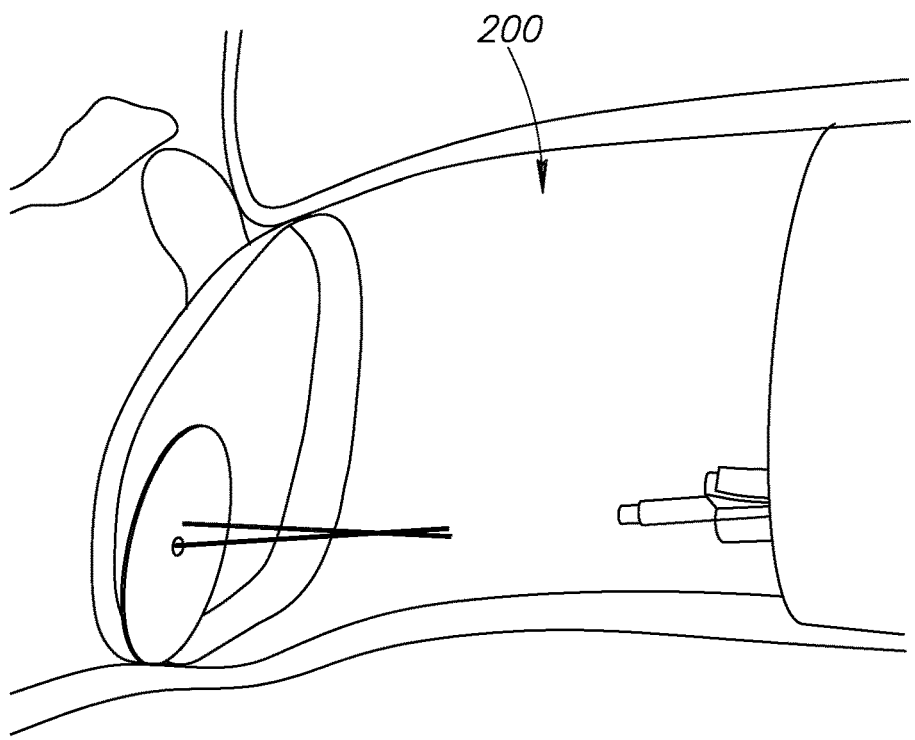

Referring to FIG. 9H, actuator 834 may be pressed, exerting a tension on filaments 826D and 826D, disengaging the distal patch cord 838Db from the distal filament 826D and the proximal patch cord 838Pb from the proximal filament 826D, releasing the distal patch 808D and the proximal patch 808P from the deployment stem 804. The deployment stem 804 may be retracted from the ear canal 200 completing the deployment of the distal patch at the inner side of the tympanic membrane, and the proximal patch at the outer side of the tympanic membrane, serving to seal the perforation on both sides.

In the figures, elements are not always provided with reference numbers; a certain element, for example, may be provided with a reference number in one of more figures, and be shown without that reference number in other one or more figures—merely for reasons of brevity. Since all figures in this application show the same device, it is intended that an element having the same shape and appearing in different figures, sometimes with a reference number and sometimes not—be interpreted as the same element.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore may include structure, acts or details of structures and acts that may not be essential to the invention and which are described as examples. Structure compounds and acts described herein are replaceable by equivalents which perform the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

What is claimed is:

1. A tympanoplatic patch applicator comprising:
   a handle disposed with a deployment control;
   a deployment stem comprising multiple nested sleeves connected to the handle;
   a patch configured to be affixed to a distal end of the deployment stem via an actuation filament disposed in the deployment stem; and
   a filament-based deployment system controllable by the deployment control, wherein the deployment stem is configured to position the patch at an internal side of a perforated tympanic membrane in a middle ear by introducing the patch into an ear canal and penetrating the perforated tympanic membrane with the distal end of the deployment stem, and wherein the filament-based deployment system is configured to release the patch from the distal end of the deployment stem, thereby deploying the patch on an internal side of the perforated tympanic membrane, wherein the multiple nested sleeves include: (a) an inner sleeve, wherein the actuation filament is disposed within the inner sleeve; and (b) a middle sleeve, having a serrated distal end that secures the position of the patch and prevents a rotation of said patch with respect to the middle sleeve, and wherein a first activation of the deployment control causes the serrated distal end of the middle sleeve to withdraw proximally from the patch, thereby releasing the patch from the serrated distal end of the middle sleeve.

2. The tympanoplatic patch applicator of claim 1, wherein the serrated distal end of the middle sleeve is beveled such that the patch is affixed at an angle that is non-perpendicular to a longitudinal axis of the middle sleeve, thereby allowing an orientation of the patch to align with an orientation of the perforated tympanic membrane.

3. The tympanoplatic patch applicator of claim 2, further comprising a posture adjustor configured with the handle, wherein the posture adjustor is configured to align the orientation of the patch with the orientation of the perforated tympanic membrane.

4. The tympanoplatic patch applicator of claim 3, wherein the deployment stem is bent, and further comprises a first spring configured to transfer an adjustment of the posture adjustor to a corresponding adjustment of the orientation of the patch over a bend of the deployment stem.

5. The tympanoplatic patch applicator of claim 1, wherein the filament-based deployment system comprises an exposable distal end of the inner sleeve, wherein the patch comprises a proximally positioned cord configured to extend from the serrated distal end of the middle sleeve inwards along the deployment stem and engage with the actuation filament at the exposable distal end of the inner sleeve, thereby affixing the patch at the serrated distal end of the middle sleeve when the exposable distal end of the inner sleeve is encased within the middle sleeve, and
   wherein a second activation of the deployment control causes the middle sleeve to withdraw proximally with respect to the inner sleeve and expose the exposable distal end, allowing the proximally positioned cord to disengage from the actuation filament to release the patch from the tympanoplatic patch applicator.

6. The tympanoplatic patch applicator of claim 5, wherein a proximal end of the proximally positioned cord comprises a first bulge, and a distal end of the actuation filament comprises a second bulge, wherein positioning the first bulge proximal to the second bulge at the exposable distal end of the inner sleeve engages the proximally positioned cord with the actuation filament, and wherein exposing the exposable distal end of the inner sleeve allows the first bulge to slide distally over the second bulge, thereby disengaging the cord from the actuation filament.

7. The tympanoplatic patch applicator of claim 1, further comprising a debridement mechanism, comprising:
   a debridement actuator configured with the handle,
   an outer sleeve of the multiple nested sleeves encasing the middle sleeve, and
   at least one protruding blade disposed at a distal end of the outer sleeve,
   wherein the debridement actuator is configured to advance the outer sleeve relative to the middle sleeve until the at least one protruding blade reaches the distal end of the deployment stem, rotate the outer sleeve relative to the middle sleeve, thereby rotating the at least one protruding blade and causing a debridement of a circumference of a perforation, and retract the outer sleeve relative to the middle sleeve.

8. The tympanoplatic patch applicator of claim 7, wherein the debridement mechanism further comprises a niche configured to collect debrided tissue.

9. The tympanoplatic patch applicator of claim 7, wherein the debridement mechanism further comprises a penetration depth controlling mechanism that limits a penetration depth of the at least one protruding blade by limiting an advancement of the outer sleeve relative to the middle sleeve.

10. The tympanoplatic patch applicator of claim 7, wherein the deployment stem is bent, and wherein the debridement actuator is configured to advance and retract the outer sleeve relative to the middle sleeve over a bend of the deployment stem.

11. The tympanoplatic patch applicator of claim 10, wherein the deployment stem further comprises a second spring configured to transfer a motion of the debridement actuator to the outer sleeve over the bend of the deployment stem, thereby enabling an advancement and a retraction of the outer sleeve relative to the middle sleeve over the bend.

12. The tympanoplatic patch applicator of claim 1, wherein the patch is constructed from a resilient material that flexes to fit through a perforation, and restores an original shape of said patch when emerging in a middle ear at an internal side of the perforated tympanic membrane.

13. A method for deploying a patch at an internal side of a perforated tympanic membrane, comprising:
   introducing the patch, affixed to the distal end of the deployment stem of the tympanoplatic patch applicator of claim 1, into an ear canal;
   penetrating a perforation of a tympanic membrane with the patch;
   using the deployment control provided with the handle of the tympanoplatic patch applicator to maneuver the filament-based deployment system that releases the patch from the distal end of the deployment stem at the internal side of the tympanic membrane; and
   deploying the patch on the internal side of the perforated tympanic membrane.

14. The method of claim 13, further comprising, while the patch is positioned at the internal side of the tympanic membrane, aligning an orientation of the patch with an orientation of the perforated tympanic membrane by rotating a posture adjustor to rotate the middle sleeve of the tympanoplatic patch applicator, wherein the patch is secured to a beveled distal end of the middle sleeve.

15. The method of claim 13, further comprising activating a debriding actuator disposed with the handle of the tympanoplatic patch applicator to advance at least one debridement blade to a distal end of the deployment stem, and rotate the at least one debridement blade about a circumference of the perforation.

16. The method of claim 15, further comprising collecting a removed tissue in a niche of the tympanoplatic patch applicator, and preventing the removed tissue from reaching a middle ear.

17. The method of claim 13, wherein deploying comprises pulling the patch proximally to come into contact with the internal side of the tympanic membrane by pulling the tympanoplatic patch applicator proximally, and securing the patch to the tympanic membrane using a fresh blood as a glue.

18. The method of claim 17, wherein using the deployment control to maneuver the filament-based deployment system comprises decoupling a cord of the patch from a filament of the tympanoplatic patch applicator in a second detachment stage.

* * * * *